United States Patent
Drahos et al.

(10) Patent No.: US 11,883,443 B2
(45) Date of Patent: Jan. 30, 2024

(54) COMPOSITIONS AND METHODS FOR IMPROVING THE HEALTH OF AQUATIC ANIMALS

(71) Applicant: Novozymes A/S, Bagsvaerd (DK)

(72) Inventors: David Drahos, Roanoke, VA (US);
Christian Munch, Frederiksberg (DK);
Lene Venke Kofod, Uggerloese (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/779,116

(22) PCT Filed: Apr. 9, 2014

(86) PCT No.: PCT/US2014/033513
§ 371 (c)(1),
(2) Date: Sep. 22, 2015

(87) PCT Pub. No.: WO2014/169046
PCT Pub. Date: Oct. 16, 2014

(65) Prior Publication Data
US 2016/0051599 A1 Feb. 25, 2016

Related U.S. Application Data

(60) Provisional application No. 61/809,986, filed on Apr. 9, 2013.

(51) Int. Cl.
| | | |
|---|---|---|
| A61K 35/742 | (2015.01) | |
| A23K 40/25 | (2016.01) | |
| C12N 1/20 | (2006.01) | |
| A23K 10/18 | (2016.01) | |
| A23K 50/80 | (2016.01) | |
| A23K 40/20 | (2016.01) | |
| A61K 9/00 | (2006.01) | |
| A61K 35/741 | (2015.01) | |
| C12R 1/07 | (2006.01) | |
| C12R 1/09 | (2006.01) | |
| C12R 1/10 | (2006.01) | |
| C12R 1/11 | (2006.01) | |
| C12R 1/12 | (2006.01) | |
| C12R 1/125 | (2006.01) | |

(52) U.S. Cl.
CPC ............ *A61K 35/742* (2013.01); *A23K 10/18* (2016.05); *A23K 40/20* (2016.05); *A23K 40/25* (2016.05); *A23K 50/80* (2016.05); *A61K 9/0056* (2013.01); *A61K 35/741* (2013.01); *C12N 1/20* (2013.01); *C12N 1/205* (2021.05); *C12R 2001/07* (2021.05); *C12R 2001/09* (2021.05); *C12R 2001/10* (2021.05); *C12R 2001/11* (2021.05); *C12R 2001/12* (2021.05); *C12R 2001/125* (2021.05)

(58) Field of Classification Search
CPC .. A61K 35/742; A61K 35/741; A61K 9/0056; A23K 40/25; A23K 50/80; A23K 10/18; A23K 40/20; C12R 1/07; C12R 1/12; C12R 1/11; C12R 1/10; C12R 1/09; C12R 1/125; C12R 1/20
See application file for complete search history.

(56) References Cited

U.S. PATENT DOCUMENTS

| | | | | |
|---|---|---|---|---|
| 4,919,936 | A * | 4/1990 | Iwanami | C12R 1/125 424/442 |
| 5,840,312 | A * | 11/1998 | Mock | A61K 39/07 424/200.1 |
| 6,878,373 | B2 | 4/2005 | Keeton | |
| 9,228,284 | B2 * | 1/2016 | McHatton | A61L 9/013 |
| 2004/0009160 | A1 * | 1/2004 | Villamar | A61K 31/365 424/93.46 |
| 2005/0031732 | A1 | 2/2005 | Suhr-Jessen | |
| 2005/0220778 | A1 | 10/2005 | Keeton | |
| 2008/0008798 | A1 * | 1/2008 | Gloor | A23K 20/105 426/321 |
| 2010/0092428 | A1 | 4/2010 | Schmidt | |
| 2011/0230245 | A1 | 9/2011 | Carr | |
| 2012/0100589 | A1 | 4/2012 | Rhine | |
| 2012/0207699 | A1 * | 8/2012 | McHatton | A61L 9/013 424/76.8 |
| 2012/0328572 | A1 | 12/2012 | Terhune | |

FOREIGN PATENT DOCUMENTS

| | | | | |
|---|---|---|---|---|
| WO | WO-2007035112 A1 * | 3/2007 | | A23K 10/14 |
| WO | 2008/021761 A2 | 2/2008 | | |
| WO | 2008/118749 A2 | 10/2008 | | |
| WO | 2009/158617 A1 | 12/2009 | | |
| WO | 2010/104794 A2 | 9/2010 | | |
| WO | 2011/059963 A1 | 5/2011 | | |
| WO | 2011/163500 A2 | 12/2011 | | |
| WO | WO-2012062895 A1 * | 5/2012 | | A61K 35/744 |
| WO | 2012/112718 A1 | 8/2012 | | |

(Continued)

OTHER PUBLICATIONS

Aly et al., Fish & Shellfish Immunology (2008) 25, 128-136.*
Ghosh et al., Aquaculture Research, 2007, 38, 518-526.*
Kumar et al., Fish & Shellfish Immunology (2008) 24, 168-172.*
Gunther et al., Int. J. Trop. Boil., vol. 52(4), pp. 937-943.*
He et al. (2011) J. Aquac. Res. Development (https://www.omicsonline.org/open-access/evaluation-of-probiotic-strain-bacillus-subtilis-C3102-as-a-feed-supplementfor-koi-carp-cyprinus-carpio-2155-9546-S1-005.php?aid=62519), accessed Nov. 13, 2017.*
"stable." The Merriam-Webster Dictionary. 2020. [retrieved on Sep. 30, 2020] <https://www.merriam-webster.com/dictionary/stable>. (Year: 2020).*

(Continued)

*Primary Examiner* — David W Berke-Schlessel
*Assistant Examiner* — Susan E. Fernandez
(74) *Attorney, Agent, or Firm* — Adam L. Rucker

(57) ABSTRACT

The present invention relates to compositions and methods for increasing the health of aquatic animals comprising one or more selected bacterial strains.

24 Claims, 1 Drawing Sheet

(56) References Cited

FOREIGN PATENT DOCUMENTS

WO    2013/096369 A1    6/2013

OTHER PUBLICATIONS

Kouimtzi, M et al. Survival of bacteria during extrusion-spheronization. Pharmaceutical Sciences. 1997. 3: 347-351. (Year: 1997).*
Balcazar et al., Curr. Microbiol., vol. 55, pp. 409-412 (2007).
Farzanfar et al., FEMS Immunol. Med. Microbiol., vol. 48, pp. 149-158 (2006).
Li et al., Journal of Dalian Fisheries University, vol. 27, No. 3, pp. 48-52 (2012).
Shen et al., Acta Hydrobiologica Sinica, vol. 37, No. 1, pp. 221-224 (2013).
Zhang et al., Handbook for the Use of Biological Pesticides, p. 178 (2011).
Anastassiadou et al; 2021, EJ EFSA Journal, vol. 19, (1) pp. 1-20.
Bampidis et al; 2020, EF EFSA Journal vol. 18, (11) pp. 1-9.
Bampidis et al; 2019, EJ EFSA Journal, vol. 17, (3) pp. 1-9.
Rychen et al.; 2018, EJ EFSA Journal, vol. 16, (3) pp. 1-9.

* cited by examiner

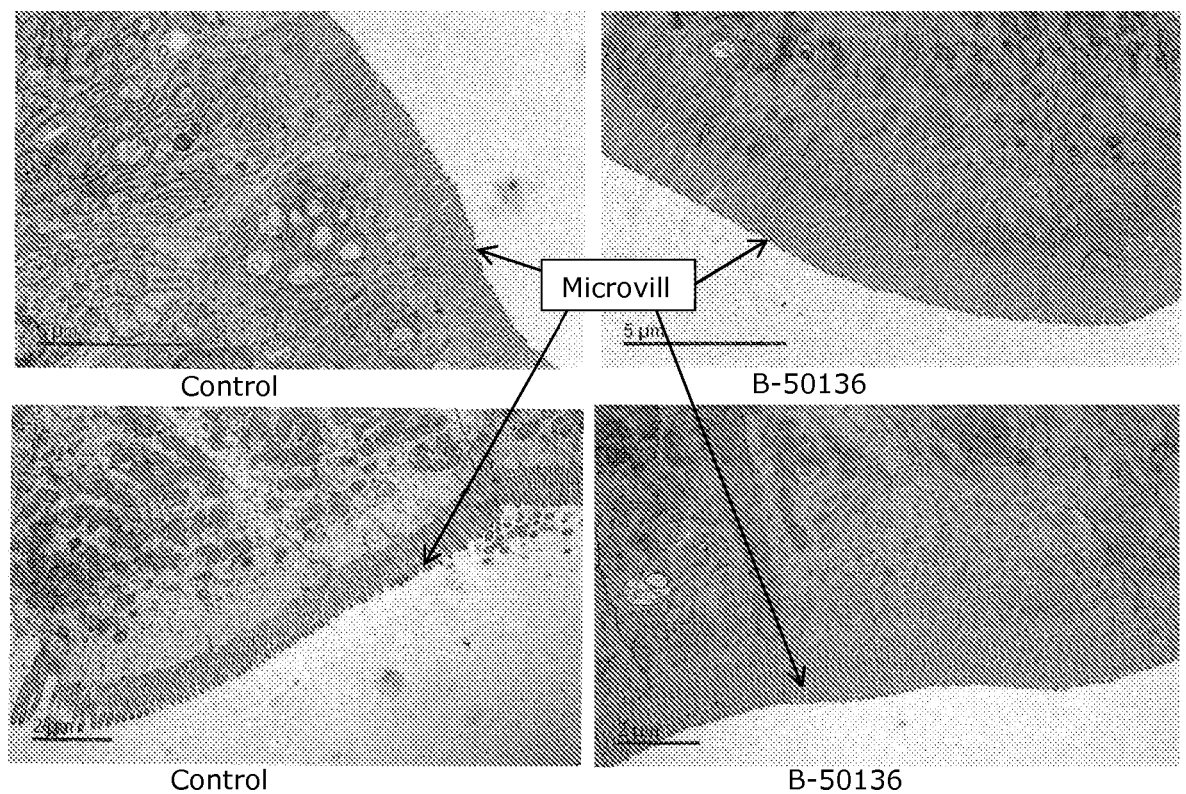

COMPOSITIONS AND METHODS FOR IMPROVING THE HEALTH OF AQUATIC ANIMALS

CROSS-REFERENCE TO RELATED APPLICATIONS

This application is a 35 U.S.C. 371 national application of PCT/US2014/033513 filed Apr. 9, 2014, which claims priority or the benefit under 35 U.S.C. 119 of U.S. provisional application No. 61/809,986 filed Apr. 9, 2013. The content of each application is fully incorporated herein by reference.

FIELD OF THE INVENTION

This application disclosed methods and compositions comprising one or more bacteria for improving the well-being, general condition or health of aquatic animals.

BACKGROUND OF THE INVENTION

Commercial fishing, the practice of catching fish and other seafood from wild fisheries for commercial profit, has raised concerns about the sustainability of wild fish populations. As such, aquaculture has emerged as a viable alternative to large scale commercial fishing. Aquaculture, or aquafarming, is the cultivation of freshwater and saltwater populations under controlled conditions and has been found to be beneficial as they reduce the impacts and pressures of commercial fishing on wild fisheries as well as reduce the human ingestion of toxins (e.g., heavy metals such as mercury) which are often found in wild caught fish such as tuna. In spite of the positive effects aquafarming has had on wild fisheries, challenges remain in the aquaculture industry. In particular, maintaining a healthy gut in the aquatic animal can improve aquatic animal weight and/or aquatic animal yields. Another major challenge throughout the industry is loss of yield due to pathogenic microorganisms which infect and cause death or illness to the aquatic animal. As such, in the aquaculture industry it remains common practice to use antibiotics to treat aquatic animals and/or environments infected by pathogenic microorganisms; however, the growing concerns regarding antibiotic resistance has created a need for new solutions for improving aquatic animal health and controlling infection from pathogenic bacteria in the aquatic animal farming (aquaculture) industry.

U.S. Pat. No. 6,878,373 discloses a composition and method for reducing the levels of pathogenic bacteria in an aquatic environment. The composition includes isolated *Bacillus cereus* which are able to reduce a number of well-known pathogenic bacterium from aquatic environments. The preferred *Bacillus cereus* is strain NRRL B-30535.

U.S. Patent Application Publication Number No.: 2010/00092428 discloses a method for enhancing the health of an animal comprising administering to the animal a composition comprising *Bacillus subtilis* QST 713 or a mutant thereof.

U.S. Patent Application Publication Number No.: 2005/0220778 discloses a composition and method for reducing the levels of pathogenic bacteria in an aquatic environment. The composition includes isolated *Bacillus cereus* which is able to reduce a number of well-known pathogenic bacterium from aquatic environments.

U.S. Patent Application Publication Number No.: 2005/0031732 discloses an aquatic animal feed product comprising a probiotic *Bacillus licheniformis* bacteria and the use of this product in an aquaculture of aquatic animals in order to improve the resistance of an aquatic animal towards influential conditions in the surrounding environment, such as e.g. pathogenic micro-organisms.

Balcazar, J. A. and Rojas-Luna, T. "Inhibitory Activity of Probiotic *Bacillus subtilis* UTM 126 Against *Vibrio* Species Confers Protection Against Vibriosis in Juvenils Shrimp (*Litopenaeus vannamei*)". Curr. Microbiol. (2007) 55: 409-412 discloses that the bacterial strain *B. subtilis* UTM 126 produced antimicrobial activity against pathogenic species of *Vibrio*.

Farzanfar, A. "Mini Review The use of probiotics in shrimp aquaculture" FES Iminol. Med. Microbiol. (2006) 48: 149-158 discloses that biologically friendly agents such as lactic acid bacteria and *Bacillus* spp. can be introduced into a culture environment to control and compete with pathogenic bacteria as well as to promote the growth of the cultured organisms.

While solutions for improving the health of animals, and aquatic animals in particular exist, a need still exists for better treatment options.

The bacterial strains indicated in this application have been disclosed in various earlier patent applications as indicated below:

WO 2008/021761 mentions strain PTA-7547. The application relates to compositions comprising selected whole bacteria cultures. The bacteria are isolated from their natural environment. The composition of the invention may be used for washing especially laundry and newly manufactured fabrics and cleaning surfaces such as carpets. A composition may optionally be supplemented with surfactants and/or other active ingredients, such as enzymes. WO 2008/118749 mentions strain PTA-7547. The application relates to methods and compositions for reducing and/or preventing biofilm formation and/or planktonic proliferation in aqueous environments. WO 2009/158617 mentions accession number NRRL B-50141. The application relates to *Bacillus amyloliquefaciens* strain NRRL B-50141, compositions comprising the *Bacillus amyloliquefaciens* strain, and deodorizing liquid compositions which are designed to be applied in the areas of pet care, toilet care, carpet care, and garbage collections or processes, management of industrial wastes. US-2011-0230245 mentions accession number NRRL B-50349. The application relates to *Bacillus amyloliquefaciens* strain NRRL B-50349, compositions comprising the *Bacillus amyloliquefaciens* strain, and its use to control the growth of fungal and bacterial organisms, as a drain opener, and in a sanitizer formulation. WO 2010/104794 mentions accession numbers NRRL B-50136, NRRL B-50016, NRRL B-50141, NRRL B-50151. The application relates to a method for treatment of a material comprising lignocellulosic fibres comprising the steps of: (i) providing a material comprising lignocellulosic fibres; (ii) inoculating the material from step a with one or more microorganisms; and (iii) incubating the material under aerobic conditions. WO 2011/059963 mentions strains NRRL B-50136, NRRL B-50016, NRRL B-50017, NRRL B-50141, PTA-7547, NRRL B-50304 and NRRL B-50349. The application relates to a method of improving permeability or flux of a membrane used in a process, comprising subjecting the membrane to one or more microorganisms capable of reducing or preventing the development of undesirable biofilm on the membrane. WO 2011/163500 mentions accession numbers NRRL B-50136, NRRL B-50016, RRL B-50017, PTA-7547, NRRL B-50304. The application relates to a method of inhibiting production of body malodor caused by bacteria by contacting the malodor-causing bacteria with at least one species of *Bacillus* or a substance derived therefrom. WO 2012/112718 mentions strain PTA-7547. The application relates to methods and compositions for inhibiting malodor in a cleaning machine, cleaning process or article treated (cleaned) in a cleaning machine or cleaning process, comprising contacting a cleaning machine, cleaning process and/or article treated in the cleaning machine/process with at least one microorganism which is able to inhibit malodor caused by a malodor causing microorganism (e.g., bacteria) present in the cleaning machine, cleaning process or article treated in the cleaning machine or cleaning process. The malodor source may be at least one malodor causing microorganism (e.g., bacteria) and/or the at least one microorganism (e.g., bacteria) capable of causing malodor. WO 2013/096369 mentions accession numbers NRRL B-50136, NRRL B-50622, NRRL B-50605, NRRL B-50606, NRRL B-50607, PTA-7547. The application relates to a process of producing an animal feed comprising treatment of a cellulosic material which increases the digestibility of the cellulosic material.

SUMMARY OF THE INVENTION

Described and disclosed herein are bacterial strains for improving the well-being, general condition or health and/or yields of aquatic animals, improving the weight of aquatic animals, improving the overall gut health of aquatic animals, and controlling pathogenic microorganisms (e.g., *Vibrio, Aeromonas, Serratia* etc.). It is an object of the embodiments disclosed herein, that the bacterial strains provided throughout will improve the health of aquatic animals.

In one embodiment, a method for improving the well-being, general condition or health of an aquatic animal is disclosed comprising administering to an aquatic animal one or more bacterial strains. In a particular embodiment, the method comprises contacting the gut of an aquatic animal with one or more bacterial strains. In a particular embodiment the bacterial strains of the methods are strains of the genus *Bacillus*. In a more particular embodiment, the one or more bacterial strains are selected from the group consisting of:

the strain having the deposit accession number NRRL B-50136;
the strain having the deposit accession number NRRL B-50622;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50606;
the strain having the deposit accession number PTA-7547;
the strain having the deposit accession number NRRL B-50304;
the strain having the deposit accession number NRRL B-50349, and combinations thereof.

In an even more particular embodiment, the bacterial strains can control species of *Vibrio, Aeromonas, Serratia* and combinations thereof.

In yet another embodiment, a composition is disclosed comprising an animal feed ingredient and one or more bacterial strains. In still another embodiment, the one or more bacterial strains are stable strains when the strains are subjected to an extrusion process having a pressure of 1 bar to 35 bar; the strains are subjected to an extrusion process wherein the extrusion process temperatures are temperatures from 80° C. to 120° C.; and the strains that control one or more pathogenic microorganisms.

In a more particular embodiment, the one or more bacterial strains are selected from the group consisting of:

the strain having the deposit accession number NRRL B-50136;
the strain having the deposit accession number NRRL B-50622;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50606;
the strain having the deposit accession number PTA-7547;
the strain having the deposit accession number NRRL B-50304;
the strain having the deposit accession number NRRL B-50349, and combinations thereof.

BRIEF DESCRIPTION OF THE FIGURES

FIG. 1 shows transmission Electron Microscopy (TEM) of Tilapia Intestinal Sections treated with NRRL B-50136 or Control Feeds (Bars note 2 µm and 5 µm lengths).

DETAILED DESCRIPTION OF THE INVENTION

The disclosed embodiments relate to compositions and methods for improving the well-being, general condition or health and/or yield of animals (e.g., aquatic animals).

Definitions

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms "a", "an" and "the" are intended to include the plural forms as well, unless the context clearly indicates otherwise.

As used herein, the terms "aquaculture", "aquaculturing", "aquafarm", and "aquafarming" can be used interchangeably and refer to the cultivation, breeding, raising, production, propagation and/or harvesting of an aquatic or marine animal, generally in an artificial environment such as a tank (e.g., an aquarium), a pond, a pool, a paddy, a lake, etc., or in an enclosed or fenced off portion of the animals natural habitat, such as a pond, a pool, a paddy, a lake, an estuary, an ocean, a marsh (e.g., a tidal marsh), a lagoon (e.g., a tidal lagoon), etc. As used herein, the term "mariculture" refers to aquaculture practiced in marine environments and in underwater habitats.

As used herein, the terms "aquatic animal", "marine animal" or "aquatic and/or marine animals" refer to organisms that live in an aquatic or marine environment. Non-limiting examples include fish, e.g., osteichthyes (including, but not limited to catfish, tilapia, trout, salmon, perch, bass, tuna, wahoo, tuna, swordfish, marlin, grouper, sturgeon, snapper, eel and walleye) and chondrichthyes (including, but not limited to sharks, rays, and skates), crustaceans (including, but not limited to crabs, lobsters, crayfish, shrimp, krill, and prawn) and mollusks (including, but not limited to snails, slugs, conch, squid, octopus, cuttlefish, clams, oysters, scallops, and mussels).

As used herein, the term "gut" is meant to refer to the gastrointestinal or digestive tract and it refers to the system of organs within multicellular animals which takes in food, digests it to extract energy and nutrients, and expels the remaining waste.

As used herein, the term "gut microflora" is intended to refer to beneficial and/or potentially beneficial bacteria in the gut. Non-limiting examples include beneficial species of Lactobacilli, Bifidobacteria, Bacillius, etc.

As used herein, the terms "administer", "administered", or "administering", is intended to mean bringing an animal, tissue, organ, and/or cell(s) into contact with a composition as described herein.

As used herein, the term "control" or "controlling" as in. e.g., the phrase: the "control" of pathogenic microorganisms, or "controlling" pathogenic microorganisms, or as in the phrase: "controlling" species of pathogenic microorganisms, refers to any means for preventing infection by pathogenic microorganisms, reducing the number of pathogenic microorganisms, killing the pathogenic microorganisms, or elimination the pathogenic microorganisms as defined herein. Indeed, "control" or "controlling" as used herein refers to any indicia of success in prevention, killing, elimination, reduction or amelioration of one or more pathogenic bacteria.

As used herein, the terms "spore" and "endospore" are interchangeable and have their normal meaning which is well known and understood by those of skill in the art. As used herein, the term spore refers to a microorganism in its dormant, protected state.

As used herein, "stable" is a term that is known in the art, and in a preferred aspect, stable is intended to mean the ability of the microorganism to remain in a spore form until it is administered to an animal to improve the health of the animal.

As used herein, the term "isolated" means that the one or more bacterial strains described herein are in a form or environment which does not occur in nature, that is, the one or more bacterial strains are at least partially removed from one or more or all of the naturally occurring constituents with which it is associated in nature.

As used herein, the term "blend" means more than one of the bacterial strains described herein.

As used herein, the term "pathogenic microorganism" means any microorganism that can adversely affect the health, yield, or environment of one or more aquatic animals.

As used herein, the term "health" refers to the state or condition of an organism or one of its parts.

As used herein, the terms "effective amount", "effective concentration", or "effective dosage" are defined as the amount, concentration, or dosage of the bacterial strain(s) sufficient to improve the health or yield of an aquatic animal. The actual effective dosage in absolute numbers depends on factors including: the state of health of the aquatic animal in question; whether the aim is prevention or reduction of a pathogenic organism, to improve overall health, gut health, etc.; other ingredients present, and also the surface or aqueous environment in question. In an embodiment an effective dosage of bacteria, e.g., of the one or more of the thirteen *Bacillus* strains disclosed, would be in the range from $1\times10^2$ to $1\times10^{12}$ CFU/g of the composition, preferably $1\times10^4$ to $1\times10^9$ CFU/g of the composition, more preferably $1\times10^5$ to $1\times10^8$ CFU/g of the composition, and even more preferably $1\times10^6$ to $5\times10^8$ CFU/g of the composition. Further, in an embodiment the ratio between the bacteria strain or blends concerned herein and the undesired microorganism(s) in question may be between 1:100,000 and 100,000:1 (strain/blend:undesired microorganism), preferably 1:10,000 to 10,000:1, more preferably 1:1,000 to 1,000:1, more preferably 1:100 to 100:1, even more preferably 1:10 to 10:1. The "effective amount", "effective concentration", or "effective dosage" of the bacterial strains may be determined by routine assays known to those readily skilled in the art.

As used herein, the term "animal feed" or "animal feed ingredient" refers to any compound, preparation, or mixture suitable for, or intended for intake by an animal.

As used herein, the term "vegetable protein(s)" refers to any compound, preparation or mixture that includes at least one protein derived from or originating from a vegetable, including modified proteins and protein-derivatives.

As used herein, the terms "pellets" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

As used herein, the term "composition" refers to a composition comprising a carrier and at least one bacterial strain as described herein. The compositions described herein may be mixed with an animal feed(s) and referred to as a "mash feed."

Compositions:

The compositions described herein comprise a carrier and one or more bacterial strains. In an embodiment, the compositions described herein can be of any form so long as the carrier is able to support the one or more bacterial strains, regardless of form (e.g., a vegetative state or a dormant state), and the composition is suitable for intake by an aquatic animal. In certain embodiments, the composition may be in the form of a liquid, a slurry, a solid, or a powder (wettable powder or dry powder). In a particular embodiment, the composition disclosed herein, regardless of form, e.g., a liquid, slurry, or powder (e.g., wettable powder or dry powder), is suitable for use as an ingredient in an animal feed. In a more particular embodiment, the compositions described herein are suitable for use as an ingredient in a pelleted animal feed. In still a more particular embodiment, the compositions described herein are suitable for use as an ingredient in an animal feed produced via an extrusion process(es).

Carrier(s):

The carriers described herein will allow the one or more bacterial strains described herein to remain efficacious (e.g., capable of improving aquatic animal well-being, general condition or health) and viable once formulated. Non-limiting examples of carriers described herein include liquids, slurries, or solids (including wettable powders or dry powders).

In one embodiment, the carrier is a liquid carrier. Non-limiting examples of liquids useful as carriers for the compositions disclosed herein include water, aqueous solutions, or non-aqueous solutions. In one embodiment, the carrier is water. In another embodiment the carrier is an aqueous solution, such as sugar water. In another embodiment, the carrier is a non-aqueous solution. If a liquid carrier is used, the liquid (e.g., water) carrier may further include growth media to culture the one or more bacterial strains. Non-limiting examples of suitable growth media for the deposited bacterial strains include arabinose-gluconate (AG), yeast extract mannitol (YEM), G16 media, or any media known to those skilled in the art to be compatible with, and/or provide growth nutrients to the one or more bacterial strains.

In another embodiment, the carrier is a slurry.

In another embodiment, the carrier is a solid. In a particular embodiment the solid is a powder. In one embodiment the powder is a wettable powder. In another embodiment, the powder is a dry powder. In another embodiment, the solid is a granule. Non-limiting examples of solids useful as carriers for the compositions disclosed herein include calcium carbonate, sodium bicarbonate, sodium chloride, peat, wheat, wheat chaff, ground wheat straw, bran, vermiculite, cellulose, starch, soil (pasteurized or unpasteurized), gypsum, talc, clays (e.g., kaolin, bentonite, montmorillonite), and silica gels. In a particular embodiment, the carrier is calcium carbonate. In another embodiment, the carrier is sodium bicarbonate.

Bacterial Strain(s):

The composition as described herein comprises one or more bacterial strains. In one embodiment, the one or more bacterial strains may be any bacterial strain that can improve the health of an aquatic animal.

In an embodiment, the one or more bacterial strains is a gram-positive bacterial strain.

In still another embodiment, the one or more bacterial strains is a gram-negative bacterial strain.

In yet another embodiment, the one or more bacterial strains is a combination of gram-positive and gram-negative bacterial strains.

In an embodiment, the one or more bacterial strains are stable when the strains are subjected to a feed manufacturing process. In a particular embodiment, the one or more strains are stable when the strains are subjected to an extrusion process for pelleting.

In one embodiment, the one or more bacterial strains are stable when subjected to pressures achieved during an extrusion process for pelleting. In a particular embodiment, the one or more bacterial strains are stable at pressures ranging from 1 bar to 40 bar, particularly 10 bar to 40 bar, more particularly 15 bar to 40 bar, even more particularly 20 bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 80° C. to 120° C., particularly temperatures ranging from 90° C. to 120° C., even more particularly temperatures ranging from 95° C. to 120° C.

In a further particular embodiment the extrusion stability of the bacterial strain(s) is determined by extrusion at 100° C. or 110° C., exhibiting 50% or more survival at 100° C. or 25% or more survival at 110° C.

In an even more particular embodiment, the one or more bacterial strains are stable when the strains are subjected to an extrusion process wherein the extruder has a die diameter of 0.5 mm to 5.0 mm.

In another embodiment, the one or more bacterial strains control one or more pathogenic microorganisms.

In still another embodiment, the one or more bacterial strains are stable strains when the strains are subjected to an extrusion process having a pressure of 1 bar to 40 bar; the strains are subjected to an extrusion process wherein the extrusion process temperatures are temperatures from 80° C. to 120° C.; and the strains control one or more pathogenic microorganisms.

In an embodiment, the one or more bacterial strains is a strain of *Agrobacterium* spp., e.g., *Agrobacterium atlanticum*; *Agrobacterium rubi*; *Agrobacterium tumefaciens*; or *Agrobacterium vitis*, and combinations thereof.

In another embodiment, the one or more bacterial strains is a strain of *Arthrobacter* spp., e.g., *Arthrobacter oxydans*; *Arthrobacter aurescens*; *Arthrobacter globiformis*; *Arthrobacter ramosus*; or *Arthrobacter viscosus*, and combinations thereof.

In another embodiment, the one or more bacterial strains is a strain of *Bacillus* spp., e.g., *Bacillus alcalophilus*, *Bacillus alvei*, *Bacillus aminovorans*, *Bacillus amyloliquefaciens*, *Bacillus aneurinolyticus*, *Bacillus aquaemaris*, *Bacillus atrophaeus*, *Bacillus boroniphilius*, *Bacillus brevis*, *Bacillus caldolyticus*, *Bacillus centrosporus*, *Bacillus cereus*, *Bacillus circulans*, *Bacillus coagulans*, *Bacillus firmus*, *Bacillus flavothermus*, *Bacillus fusiformis*, *Bacillus globigii*, *Bacillus infernus*, *Bacillus larvae*, *Bacillus laterosporus*, *Bacillus lentus*, *Bacillus licheniformis*, *Bacillus megaterium*, *Bacillus*, *mesentericus*, *Bacillus mucilaginosus*, *Bacillus mycoides*, *Bacillus natto*, *Bacillus pantothenticus*, *Bacillus polymyxa*, *Bacillus pseudoanthracis*, *Bacillus pumilus*, *Bacillus schlegelii*, *Bacillus sphaericus*, *Bacillus sporothermodurans*, *Bacillus stearothermophillus*, *Bacillus subtilis*, *Bacillus thermoglucosidasius*, *Bacillus thuringiensis*, *Bacillus vulgatis*, *Bacillus weihenstephanensis*, and combinations thereof.

In another embodiment, the one or more bacterial strains is a strain of *Bacteroides* spp., e.g., *Bacteroides cellulosolvens*; *Bacteroides galacturonicus*; *Bacteroides pectinophilus*; or *Bacteroides* vulgates, and combinations thereof.

In another embodiment, the one or more bacterial strains is a strain of *Beggiatoa* spp., e.g., *Beggiatoa alba*, and combinations thereof.

In another embodiment, the one or more bacterial strains is a strain of *Beijerinckia* spp., e.g., *Beijerinckia derxia*; *Beijerinckia fluminensis*; *Beijerinckia indica*; or *Beijerinckia mobilis*, and combinations thereof.

In another embodiment, the one or more bacterial strains is a strain of *Bifidobacterium* spp., e.g., *Bifidobacterium animalis*; *Bifidobacterium inducum*; *Bifidobacterium magnum*; *Bifidobacterium minimum*; or *Bifidobacterium subtile*, and combinations thereof.

In another embodiment, the one or more bacterial strains is a strain of *Brachybacterium* spp., e.g., *Brachybacterium alimentarium*; *Brachybacterium nesterenkovii*; or *Brachybacterium rhamnosum*, and combinations thereof.

In another embodiment, the one or more bacterial strains is a strain of *Bradyrhizobium* spp., e.g., *Bradyrhizobium elkanii*; *Bradyrhizobium japonicum*; or *Bradyrhizobium liaoningense*, and combinations thereof.

In another embodiment, the one or more bacterial strains is a strain of *Brevibacillus* spp., e.g., *Brevibacillus brevis*; *Brevibacillus formosus*; *Brevibacillus laterosporus*; or *Brevibacillus parabrevis*, and combinations thereof.

In another embodiment, the one or more bacterial strains is a strain of *Burkholderia* spp., e.g., *Burkholderia andropogonis*; *Burkholderia sacchari*; or *Burkholderia vandii*, and combinations thereof.

In another embodiment, the one or more bacterial strains is a strain of *Carnobacterium* spp., e.g., *Carnobacterium divergens*; *Carnobacterium funditum*; *Carnobacterium mobile*; or *Carnobacterium pleistocenium*, and combinations thereof.

In another embodiment, the one or more bacterial strains is a strain of *Caulobacter* spp., e.g., *Caulobacter bacteriodes*; *Caulobacter fusiformis*; *Caulobacter variabilis*; or *Caulobacter viriodoes*, and combinations thereof.

In another embodiment, the one or more bacterial strains is a strain of *Cellulomonas* spp., e.g., *Cellulomonas humilata* or *Cellulomonas xylanilitica*, and combinations thereof.

In another embodiment, the one or more bacterial strains is a strain of *Citrobacter* spp., e.g., *Citrobacter amalonaticus*; *Citrobacter koseri*; or *Citrobacter freundii*, and combinations thereof.

In another embodiment, the one or more bacterial strains is a strain of *Corynebacerium* spp., e.g., *Corynebacterium flavescens* or *Corynebacterium glutamicum*, and combinations thereof.

In another embodiment, the one or more bacterial strains is a strain of *Enterobacter* spp., e.g., *Enterobacter cloacae*; *Enterobacter dissolvens*; *Enterobacter gergoviae*; *Enterobacter nimipressuralis*; or *Enterobacter pyrinus*, and combinations thereof. In another embodiment, the one or more bacterial strains is a strain of *Escherichia* spp., e.g., *Escherichia albertii*; *Escherichia blattae*; *Escherichia coli*; *Escherichia fergusonii*; *Escherichia hermannii*; or *Escherichia vluneris*, and combinations thereof.

In another embodiment, the one or more bacterial strains is a strain of *Erwinia* spp., e.g., *Erwinia amylovora* or *Erwinia caratovora*, and combinations thereof.

In another embodiment, the one or more bacterial strains is a strain of *Flavobacterium* spp., e.g., *Flavobacterium acidurans* or *Flavobacterium resinovorum*, and combinations thereof.

In another embodiment, the one or more bacterial strains is a strain of *Gluconoabacter* spp., e.g., *Gluconobacter oxidans*, and combinations thereof.

In another embodiment, the one or more bacterial strains is a strain of *Halomonas* spp., e.g., *Halomonas* elongate or *Halomonas salinas*, and combinations thereof.

In another embodiment, the one or more bacterial strains is a strain of *Hyphomicrobium* spp., e.g., *Hyphomicrobium facilis* or *Hyphomicrobium indicum*, and combinations thereof.

In another embodiment, the one or more bacterial strains is a strain of *Lactobacillus* spp., e.g., *Lactobacillus casei*; *Lactobacillus helveticus*; *Lactobacillus johnsonii*; or *Lactobacillus paracasei*, and combinations thereof.

In another embodiment, the one or more bacterial strains is a strain of *Lactococcus* spp., e.g., *Lactococcus lacti*, and combinations thereof.

In another embodiment, the one or more bacterial strains is a strain of *Leuconostoc* spp., e.g., *Leuconostoc citreum* or *Leuconostoc mesenteroides*, and combinations thereof.

In another embodiment, the one or more bacterial strains is a strain of *Lysobacter* spp., e.g., *Lysobacter antibioticus*; *Lysobacter brunescens*; or *Lysobacter enzymogenes*, and combinations thereof.

In another embodiment, the one or more bacterial strains is a strain of *Methylobacterium* spp., e.g., *Methylobacterium organophilum* or *Methylobacterium rhodesianum*, and combinations thereof.

In another embodiment, the one or more bacterial strains is a strain of *Microbacterium* spp., e.g., *Microbacterium laevaniformans* and combinations thereof.

In another embodiment, the one or more bacterial strains is a strain of *Myxococcus* spp., e.g., *Myxococcus fulvus* or *Myxococcus xanthus*, and combinations thereof.

In another embodiment, the one or more bacterial strains is a strain of *Nocardiodes* spp., e.g., *Nocardiodes oleivorans* and combinations thereof.

In another embodiment, the one or more bacterial strains is a strain of *Oceanospirillum* spp., e.g., *Oceanospirillum linum* and combinations thereof.

In another embodiment, the one or more bacterial strains is a strain of *Pediococcus* spp., e.g., *Pediococcus acidilactici* or *Pediococcus pentosaceus* and combinations thereof.

In another embodiment, the one or more bacterial strains is a strain of *Photobacterium* spp., e.g., *Photobacterium damsela* or *Photobacterium phosphoreum* and combinations thereof.

In another embodiment, the one or more bacterial strains is a strain of *Planctomyces* spp., e.g., *Planctomyces brasiliensis* or *Planctomyces maris* and combinations thereof.

In another embodiment, the one or more bacterial strains is a strain of *Polyangium* spp., e.g., *Polyangium cellulosum* and combinations thereof.

In another embodiment, the one or more bacterial strains is a strain of *Pseudoalteromonas* spp., e.g., *Pseudoalteromonas atlantica* or *Pseudoalteromonas nigrifaciens* and combinations thereof.

In another embodiment, the one or more bacterial strains is a strain of *Pseudonorcardia* spp., e.g., *Pseudonorcardia autotrophic* and combinations thereof.

In another embodiment, the one or more bacterial strains is a strain of *Paenibacillus* spp., e.g., *Paenibacillus alvei*; *Paenibacillus amylolyticus*; *Paenibacillus azotofixans*; *Paenibacillus cookii*; *Paenibacillus macerans*; *Paenibacillus polymyxa*; or *Paenibacillus validus*, and combinations thereof.

In another embodiment, the one or more bacterial strains is a strain of *Paracoccus* spp., e.g., *Paracoccus alcaliphilus*; *Paracoccus denitrificans*; *Paracoccus kocurii*; or *Paracoccus pantotrophus*, and combinations thereof.

In another embodiment, the one or more bacterial strains is a strain of *Pseudomonas* spp., e.g., *Pseudomonas anitmiicrobica*; *Pseudomonas aureofaciens*; *Pseudomonas chlororaphis*; *Pseudomonas corrugata*; *Pseudomonas fluorescens*; *Pseudomonas marginalis*; *Pseudomonas nitroreducens*; or *Pseudomonas putida*, and combinations thereof.

In another embodiment, the one or more bacterial strains is a strain of *Rhodococcus* spp., e.g., *Rhodococcus coprophilus*; *Rhodococcus erythropolis*; *Rhodococcus marinonascens*; *Rhodococcus rhodochrous*; *Rhodococcus ruber*; or *Rhodococcus zopfii*, and combinations thereof.

In another embodiment, the one or more bacterial strains is a strain of *Rhodospirillum* spp., e.g., *Rhodospirillum rubrum* and combinations thereof.

In another embodiment, the one or more bacterial strains is a strain of *Salmonella* spp., e.g., *Salmonella bongori*; or *Salmonella enterica*, and combinations thereof.

In another embodiment, the one or more bacterial strains is a strain of *Sphingomonas* spp., e.g., *Sphingomonas adhaesiva*, and combinations thereof.

In another embodiment, the one or more bacterial strains is a strain of *Stackebrandtia* spp., e.g., *Stackebrandtia nassauensis*, and combinations thereof.

In another embodiment, the one or more bacterial strains is a strain of *Streptomyces* spp., e.g., *Streptomyces aureofaciens* or *Streptomyces griseus*, and combinations thereof.

In another embodiment, the one or more bacterial strains is a strain of *Thiobacillus* spp., e.g., *Thiobacillus halophilus* or *Thiobacillus thioparus*, and combinations thereof.

In another embodiment, the one or more bacterial strains is a strain of *Agrobacterium* spp., e.g., *Agrobacterium atlanticum; Agrobacterium rubi; Agrobacterium tumefaciens;* or *Agrobacterium vitis, Arthrobacter* spp., e.g., *Arthrobacter oxydans; Arthrobacter aurescens; Arthrobacter globiformis; Arthrobacter ramosus;* or *Arthrobacter viscosus, Bacillus* spp., e.g., *Bacillus alcalophilus, Bacillus alvei, Bacillus aminovorans, Bacillus amyloliquefaciens, Bacillus aneurinolyticus, Bacillus aquaemaris, Bacillus atrophaeus, Bacillus boroniphilius, Bacillus brevis, Bacillus caldolyticus, Bacillus centrosporus, Bacillus cereus, Bacillus circulans, Bacillus coagulans, Bacillus firmus, Bacillus flavothermus, Bacillus fusiformis, Bacillus globigii, Bacillus infernus, Bacillus larvae, Bacillus laterosporus, Bacillus lentus, Bacillus licheniformis, Bacillus megaterium, Bacillus, mesentericus, Bacillus mucilaginosus, Bacillus mycoides, Bacillus natto, Bacillus pantothenticus, Bacillus polymyxa, Bacillus pseudoanthracis, Bacillus pumilus, Bacillus schlegelii, Bacillus sphaericus, Bacillus sporothermodurans, Bacillus stearothermophillus, Bacillus subtilis, Bacillus thermoglucosidasius, Bacillus thuringiensis, Bacillus vulgatis, Bacillus weihenstephanensis, Bacteroides* spp., e.g., *Bacteroides cellulosolvens; Bacteroides galacturonicus; Bacteroides pectinophilus;* or *Bacteroides vulgates, Beggiatoa* spp., e.g., *Beggiatoa alba, Beijerinckia* spp., e.g., *Beijerinckia derxia; Beijerinckia fluminensis; Beijerinckia indica;* or *Beijerinckia mobilis, Bifidobacterium* spp., e.g., *Bifidobacterium animalis; Bifidobacterium inducum; Bifidobacterium magnum; Bifidobacterium minimum;* or *Bifidobacterium subtile, Brachybacterium* spp., e.g., *Brachybacterium alimentarium; Brachybacterium nesterenkovii;* or *Brachybacterium rhamnosum, Bradyrhizobium* spp., e.g., *Bradyrhizobium elkanii; Bradyrhizobium japonicum;* or *Bradyrhizobium liaoningense, Brevibacillus* spp., e.g., *Brevibacillus brevis; Brevibacillus formosus; Brevibacillus laterosporus;* or *Brevibacillus parabrevis, Burkholderia* spp., e.g., *Burkholderia andropogonis; Burkholderia sacchari;* or *Burkholderia vandii, Carnobacterium* spp., e.g., *Carnobacterium divergens; Carnobacterium funditum; Carnobacterium mobile;* or *Carnobacterium pleistocenium, Caulobacter* spp., e.g., *Caulobacter bacteriodes; Caulobacter fusiformis; Caulobacter variabilis;* or *Caulobacter viriodoes, Cellulomonas* spp., e.g., *Cellulomonas humilata* or *Cellulomonas xylanilitica, Citrobacter* spp., e.g., *Citrobacter amalonaticus; Citrobacter koseri;* or *Citrobacter freundii, Corynebacerium* spp., e.g., *Corynebacterium flavescens* or *Corynebacterium glutamicum, Enterobacter* spp., e.g., *Enterobacter cloacae; Enterobacter dissolvens; Enterobacter gergoviae; Enterobacter nimipressuralis;* or *Enterobacter pyrinus, Escherichia* spp., e.g., *Escherichia albertii; Escherichia blattae; Escherichia coli; Escherichia fergusonii;* or *Escherichia hermannii, Erwinia* spp., e.g., *Erwinia amylovora* or *Erwinia caratovora, Flavobacterium* spp., e.g., *Flavobacterium acidurans* or *Flavobacterium resinovorum, Gluconoabacter* spp., e.g., *Gluconobacter oxidans, Halomonas* spp., e.g., *Halomonas elongate* or *Halomonas salinas, Hyphomicrobium* spp., e.g., *Hyphomicrobium facilis* or *Hyphomicrobium indicum, Lactobacillus* spp., e.g., *Lactobacillus casei; Lactobacillus helveticus; Lactobacillus johnsonii;* or *Lactobacillus paracasei, Lactococcus* spp., e.g., *Lactococcus lacti, Leuconostoc* spp., e.g., *Leuconostoc citreum* or *Leuconostoc mesenteroides, Lysobacter* spp., e.g., *Lysobacter antibioticus; Lysobacter brunescens;* or *Lysobacter enzymogenes, Methylobacterium* spp., e.g., *Methylobacterium organophilum* or *Methylobacterium rhodesianum, Microbacterium* spp., e.g., *Microbacterium laevaniformans, Myxococcus* spp., e.g., *Myxococcus fulvus* or *Myxococcus xanthus, Nocardiodes* spp., e.g., *Nocardiodes oleivorans, Oceanospirillum* spp., e.g., *Oceanospirillum linum, Pediococcus* spp., e.g., *Pediococcus acidilactici* or *Pediococcus pentosaceus, Photobacterium* spp., e.g., *Photobacterium damsela* or *Photobacterium phosphoreum, Planctomyces* spp., e.g., *Planctomyces brasiliensis* or *Planctomyces maris, Polyangium* spp., e.g., *Polyangium cellulosum, Pseudoalteromonas* spp., e.g., *Pseudoalteromonas atlantica* or *Pseudoalteromonas nigrifaciens, Pseudonorcardia* spp., e.g., *Pseudonorcardia autotrophic, Paenibacillus* spp., e.g., *Paenibacillus alvei; Paenibacillus amylolyticus; Paenibacillus azotofixans; Paenibacillus cookii; Paenibacillus macerans; Paenibacillus polymyxa;* or *Paenibacillus validus, Paracoccus* spp., e.g., *Paracoccus alcaliphilus; Paracoccus denitrificans; Paracoccus kocurii;* or *Paracoccus pantotrophus, Pseudomonas* spp., e.g., *Pseudomonas anitmiicrobica; Pseudomonas aureofaciens; Pseudomonas chlororaphis; Pseudomonas corrugata; Pseudomonas fluorescens; Pseudomonas marginalis; Pseudomonas nitroreducens;* or *Pseudomonas putida, Rhodococcus* spp., e.g., *Rhodococcus coprophilus; Rhodococcus erythropolis; Rhodococcus marinonascens; Rhodococcus rhodochrous; Rhodococcus ruber;* or *Rhodococcus zopfii, Rhodospirillum* spp., e.g., *Rhodospirillum rubrum, Salmonella* spp., e.g., *Salmonella bongori;* or *Salmonella enterica, Sphingomonas* spp., e.g., *Sphingomonas adhaesiva, Stackebrandtia* spp., e.g., *Stackebrandtia nassauensis, Streptomyces* spp., e.g., *Streptomyces aureofaciens* or *Streptomyces griseus, Thiobacillus* spp., e.g., *Thiobacillus halophilus* or *Thiobacillus thioparus*, and combinations thereof.

In a particular embodiment, the one or more bacterial strains are strains of *Bacillus amyloliquifaciens, Bacillus subtilis, Bacillus pumilus, Bacillus polymyxa, Bacillus licheniformis, Bacillus megaterium, Bacillus coagulans, Bacillus circulans*, and combinations thereof.

In a more particular embodiment, the one or more bacterial strains are selected from the group consisting of:
 the strain having the deposit accession number NRRL B-50136;
 the strain having the deposit accession number NRRL B-50622;
 the strain having the deposit accession number NRRL B-50605;
 the strain having the deposit accession number NRRL B-50016;
 the strain having the deposit accession number NRRL B-50017;
 the strain having the deposit accession number NRRL B-50141;
 the strain having the deposit accession number NRRL B-50607;
 the strain having the deposit accession number NRRL B-50151;

the strain having the deposit accession number NRRL B-50606;

the strain having the deposit accession number PTA-7547;

the strain having the deposit accession number NRRL B-50304;

the strain having the deposit accession number NRRL B-50349, and combinations thereof, including more than two, such as, at least three of the above strains, at least four of the above strains, at least five of the above strains, at least six of the above strains, at least seven of the above strains, at least eight of the above strains, at least nine of the above strains, at least ten of the above strains, at least eleven of the above strains, up to and including all of the above strains.

Specifically an embodiment features the combination of strains NRRL B-50136 and NRRL B-50622. Specifically an embodiment features the combination of strains NRRL B-50136 and NRRL B-50605. Specifically an embodiment features the combination of strains NRRL B-50136 and NRRL B-50016. Specifically an embodiment features the combination of strains NRRL B-50136 and NRRL B-50017. Specifically an embodiment features the combination of strains NRRL B-50136 and NRRL B-50141. Specifically an embodiment features the combination of strains NRRL B-50136 and NRRL B-50607. Specifically an embodiment features the combination of strains NRRL B-50136 and NRRL B-50151. Specifically an embodiment features the combination of strains NRRL B-50136 and NRRL B-50606. Specifically an embodiment features the combination of strains NRRL B-50136 and PTA-7547. Specifically an embodiment features the combination of strains NRRL B-50136 and NRRL B-50304. Specifically an embodiment features the combination of strains NRRL B-50136 and NRRL B-50349.

Specifically an embodiment features the combination of strains NRRL B-50622 and NRRL B-50605. Specifically an embodiment features the combination of strains NRRL B-50622 and NRRL B-50016. Specifically an embodiment features the combination of strains NRRL B-50622 and NRRL B-50017. Specifically an embodiment features the combination of strains NRRL B-50622 and NRRL B-50141. Specifically an embodiment features the combination of strains NRRL B-50622 and NRRL B-50607. Specifically an embodiment features the combination of strains NRRL B-50622 and NRRL B-50151. Specifically an embodiment features the combination of strains NRRL B-50622 and NRRL B-50606. Specifically an embodiment features the combination of strains NRRL B-50622 and PTA-7547. Specifically an embodiment features the combination of strains NRRL B-50622 and NRRL B-50304. Specifically an embodiment features the combination of strains NRRL B-50622 and NRRL B-50349.

Specifically an embodiment features the combination of strains NRRL B-50605 and NRRL B-50016. Specifically an embodiment features the combination of strains NRRL B-50605 and NRRL B-50017. Specifically an embodiment features the combination of strains NRRL B-50605 and NRRL B-50141. Specifically an embodiment features the combination of strains NRRL B-50605 and NRRL B-50607. Specifically an embodiment features the combination of strains NRRL B-50605 and NRRL B-50151. Specifically an embodiment features the combination of strains NRRL B-50605 and NRRL B-50606. Specifically an embodiment features the combination of strains NRRL B-50605 and PTA-7547. Specifically an embodiment features the combination of strains NRRL B-50605 and NRRL B-50304.

Specifically an embodiment features the combination of strains NRRL B-50605 and NRRL B-50349.

Specifically an embodiment features the combination of strains NRRL B-50016 and NRRL B-50017. Specifically an embodiment features the combination of strains NRRL B-50016 and NRRL B-50141. Specifically an embodiment features the combination of strains NRRL B-50016 and NRRL B-50607. Specifically an embodiment features the combination of strains NRRL B-50016 and NRRL B-50151. Specifically an embodiment features the combination of strains NRRL B-50016 and NRRL B-50606. Specifically an embodiment features the combination of strains NRRL B-50016 and PTA-7547. Specifically an embodiment features the combination of strains NRRL B-50016 and NRRL B-50304. Specifically an embodiment features the combination of strains NRRL B-50016 and NRRL B-50349.

Specifically an embodiment features the combination of strains NRRL B-50017 and NRRL B-50141. Specifically an embodiment features the combination of strains NRRL B-50017 and NRRL B-50607. Specifically an embodiment features the combination of strains NRRL B-50017 and NRRL B-50151. Specifically an embodiment features the combination of strains NRRL B-50017 and NRRL B-50606. Specifically an embodiment features the combination of strains NRRL B-50017 and PTA-7547. Specifically an embodiment features the combination of strains NRRL B-50017 and NRRL B-50304. Specifically an embodiment features the combination of strains NRRL B-50017 and NRRL B-50349.

Specifically an embodiment features the combination of strains NRRL B-50141 and NRRL B-50607. Specifically an embodiment features the combination of strains NRRL B-50141 and NRRL B-50151. Specifically an embodiment features the combination of strains NRRL B-50141 and NRRL B-50606. Specifically an embodiment features the combination of strains NRRL B-50141 and PTA-7547. Specifically an embodiment features the combination of strains NRRL B-50141 and NRRL B-50304. Specifically an embodiment features the combination of strains NRRL B-50141 and NRRL B-50349.

Specifically an embodiment features the combination of strains NRRL B-50607 and NRRL B-50151. Specifically an embodiment features the combination of strains NRRL B-50607 and NRRL B-50606. Specifically an embodiment features the combination of strains NRRL B-50607 and PTA-7547. Specifically an embodiment features the combination of strains NRRL B-50607 and NRRL B-50304. Specifically an embodiment features the combination of strains NRRL B-50607 and NRRL B-50349.

Specifically an embodiment features the combination of strains NRRL B-50151 and NRRL B-50606. Specifically an embodiment features the combination of strains NRRL B-50151 and PTA-7547. Specifically an embodiment features the combination of strains NRRL B-50151 and NRRL B-50304. Specifically an embodiment features the combination of strains NRRL B-50151 and NRRL B-50349. Specifically an embodiment features the combination of strains NRRL B-50606 and PTA-7547. Specifically an embodiment features the combination of strains NRRL B-50606 and NRRL B-50304. Specifically an embodiment features the combination of strains NRRL B-50606 and NRRL B-50349. Specifically an embodiment features the combination of strains PTA-7547 and NRRL B-50304. Specifically an embodiment features the combination of strains PTA-7547 and NRRL B-50349.

Another specific embodiment features the combination of strains NRRL B-50136, NRRL B-50622 and NRRL B-50605. All other permutations of 3, 4, 5, 6, 7, 8, 9, 10, 11 and 12 of these strains are also indicated herewith.

In a particular embodiment, the one or more bacterial strains will be present in a quantity between $1 \times 10^2$ and $1 \times 10^{12}$ CFU/g of the composition, particularly $1 \times 10^4$ and $1 \times 10^9$ CFU/g of the composition, and more particularly $1 \times 10^5$ and $5 \times 10^8$ CFU/g of the composition. In a more particular embodiment the one or more bacterial strains will be present in a quantity between $1 \times 10^6$ and $1 \times 10^8$ CFU/g of the composition.

The fermentation of the one or more bacterial strains may be conducted using conventional fermentation processes, such as, aerobic liquid-culture techniques, shake flask cultivation, and small-scale or large-scale fermentation (e.g., continuous, batch, fed-batch, solid state fermentation, etc.) in laboratory or industrial fermentors, and such processes are well known in the art. Notwithstanding the production process used to produce the one or more bacterial strains, the one or more bacterial strains may be used directly from the culture medium or subject to purification and/or further processing steps (e.g., a drying process).

Following fermentation, the one or more bacterial strains may be recovered using conventional techniques (e.g., by filtration, centrifugation, etc.). The one or more bacterial strains may alternatively be dried (e.g., air-drying, freeze drying, or spray drying to a low moisture level, and storing at a suitable temperature, e.g., room temperature).

In an embodiment, the one or more bacteria disclosed herein are stable and retain a sufficient effective amount of activity when used. Methods for producing stabilized microorganisms are known in the art. In one embodiment, the one or more bacteria disclosed herein are present in the composition in the form of a stable spore.

Optional Ingredients:

The compositions described herein may further comprise one or more optional ingredients that are suitable for consumption by an aquatic animal. Non-limiting optional ingredients include enzymes. Such ingredients are known to those skilled in the art.

Enzymes

It is further envisioned that the compositions described herein optionally include one or more enzymes as described herein. In a particular embodiment, the one or more enzymes may be any enzyme or combination of different enzymes that are suitable to be given to an animal, meaning that it in one way or the other will be good for the animal nutritionally to eat the enzyme. Accordingly, when reference is made to "an enzyme" this will in general be understood to include one or more feed enzymes. In a particular embodiment it is not construed as including enzymes which has a therapeutic function in medical sense.

The feed enzymes should be feed/food grade, thus meaning that they may not be harmful to the aquatic animal and be a feed/food grade meaning that it should comply with recommended purity specifications for food grade enzymes. In a particular embodiment this means that the enzyme complies with recommended purity specifications for food grade enzymes given by the Joint FAO/WHO Expert Committee on Food Additives (JECFA) and the Food Chemical Codex (FCC).

The enzyme shall in a particular embodiment comprise less than 30 coliform bacteria per gram and comprise a viable count of less than 50000/g.

It is to be understood that enzyme variants (produced, for example, by recombinant techniques) are included within the meaning of the term "enzyme". Examples of such enzyme variants are disclosed, e.g. in EP 251,446 (Genencor), WO 91/00345 (Novo Nordisk), EP 525,610 (Solvay) and WO 94/02618 (Gist-Brocades NV).

Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at URL: afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation", K. Ohmiya, K. Hayashi, K. Sakka, Y. Kobayashi, S. Karita and T. Kimura eds., Uni Publishers Co., Tokyo, pp. 15-23).

The types of enzymes which may be incorporated into compositions described herein include oxidoreductases (EC 1.-.-.-), transferases (EC 2.-.-.-), hydrolases (EC 3.-.-.-), lyases (EC 4.-.-.-), isomerases (EC 5.-.-.-) and ligases (EC 6.-.-.-).

Preferred oxidoreductases in the context of the compositions described herein are peroxidases (EC 1.11.1), laccases (EC 1.10.3.2) and glucose oxidases (EC 1.1.3.4). An Example of a commercially available oxidoreductase (EC 1.-.-.-) is Gluzyme™ (enzyme available from Novozymes NS). Further oxidoreductases are available from other suppliers. Preferred transferases are transferases in any of the following sub-classes:

a Transferases transferring one-carbon groups (EC 2.1);
b transferases transferring aldehyde or ketone residues (EC 2.2); acyltransferases (EC 2.3);
c glycosyltransferases (EC 2.4);
d transferases transferring alkyl or aryl groups, other that methyl groups (EC 2.5); and
e transferases transferring nitrogeneous groups (EC 2.6).

A most preferred type of transferase in the context of the compositions described herein is a transglutaminase (protein-glutamine γ-glutamyltransferase; EC 2.3.2.13).

Further examples of suitable transglutaminases are described in WO 96/06931 (Novo Nordisk NS).

Preferred hydrolases in the context of the compositions described herein are: carboxylic ester hydrolases (EC 3.1.1.-) such as lipases (EC 3.1.1.3); phytases (EC 3.1.3.-), e.g. 3-phytases (EC 3.1.3.8) and 6-phytases (EC 3.1.3.26); glycosidases (EC 3.2, which fall within a group denoted herein as "carbohydrases"), such as α-amylases (EC 3.2.1.1); peptidases (EC 3.4, also known as proteases); and other carbonyl hydrolases. Examples of commercially available phytases include Bio-Feed™ Phytase (Novozymes), Ronozyme™ product series (DSM Nutritional Products), Natuphos™ (BASF), Quantum®, Finase™ (AB Enzymes), and the AxtraPhy® and Phyzyme™ product series (Danisco). Other preferred phytases include those described in WO 98/28408, WO 00/43503, and WO 03/066847.

In the present context, the term "carbohydrase" is used to denote not only enzymes capable of breaking down carbohydrate chains (e.g. starches or cellulose) of especially five- and six-membered ring structures (i.e. glycosidases, EC 3.2), but also enzymes capable of isomerizing carbohydrates, e.g. six-membered ring structures such as D-glucose to five-membered ring structures such as D-fructose.

Carbohydrases of relevance include the following (EC numbers in parentheses): α-amylases (EC 3.2.1.1), β-amylases (EC 3.2.1.2), glucan 1,4-α-glucosidases (EC 3.2.1.3), endo-1,4-beta-glucanase (cellulases, EC 3.2.1.4), endo-1,3 (4)-β-glucanases (EC 3.2.1.6), endo-1,4-β-xylanases (EC 3.2.1.8), dextranases (EC 3.2.1.11), chitinases (EC 3.2.1.14), polygalacturonases (EC 3.2.1.15), lysozymes (EC 3.2.1.17), β-glucosidases (EC 3.2.1.21), α-galactosidases (EC 3.2.1.22), β-galactosidases (EC 3.2.1.23), amylo-1,6-glucosidases (EC 3.2.1.33), xylan 1,4-β-xylosidases (EC 3.2.1.37), glucan endo-1,3-β-D-glucosidases (EC 3.2.1.39), α-dextrin endo-1,6-α-glucosidases (EC3.2.1.41), sucrose α-glucosidases (EC 3.2.1.48), glucan endo-1,3-α-glucosidases (EC 3.2.1.59), glucan 1,4-β-glucosidases (EC 3.2.1.74), glucan endo-1,6-β-glucosidases (EC 3.2.1.75), galactanases (EC 3.2.1.89), arabinan endo-1,5-α-L-arabinosidases (EC 3.2.1.99), lactases (EC 3.2.1.108), chitosanases (EC 3.2.1.132) and xylose isomerases (EC 5.3.1.5).

In the present context a phytase is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate.

Three different types of phytases are known: a so-called 3-phytase (alternative name 1-phytase; a myo-inositol hexaphosphate 3-phosphohydrolase, EC 3.1.3.8), a so-called 4-phytase (alternative name 6-phytase, name based on 1 L-numbering system and not 1 D-numbering, EC 3.1.3.26), and a so-called 5-phytase (EC 3.1.3.72). For the purposes of the compositions described herein, all three types are included in the definition of phytase.

For the purposes of the compositions described herein phytase activity may be, preferably is, determined in the unit of FYT, one FYT being the amount of enzyme that liberates 1 micro-mol inorganic ortho-phosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are described in Example 1 of WO 00/20569. FTU is for determining phytase activity in feed and premix.

Preferred examples of phytases are microbial phytases, such as fungal or bacterial phytases, e.g., derived from the following:

i) Ascomycetes, such as those disclosed in EP 684313 or U.S. Pat. No. 6,139,902; *Aspergillus awamori* PHYA (SWISSPROT P34753, Gene 133:55-62 (1993)); *Aspergillus niger (ficuum)* PHYA (SWISSPROT P34752, Gene 127:87-94 (1993), EP 420358); *Aspergillus awamori* PHYB (SWISSPROT P34755, Gene 133:55-62 (1993)); *Aspergillus niger* PHYB (SWISSPROT P34754, Biochem. Biophys. Res. Commun. 195:53-57(1993)); *Emericella nidulans* PHYB (SWISSPROT 000093, Biochim. Biophys. Acta 1353: 217-223 (1997));

ii) *Thermomyces* or *Humicola*, such as the *Thermomyces lanuginosus* phytase disclosed in WO 97/35017;

iii) *Basidiomycetes*, such as *Peniophora* (WO 98/28408 and WO 98/28409);

iv) Other fungal phytases such as those disclosed in JP 11000164 (*Penicillium* phytase), or WO98/13480 (*Monascus anka* phytase);

v) *Bacillus*, such as *Bacillus subtilis* PHYC (SWISSPROT 031097, Appl. Environ. Microbiol. 64:2079-2085 (1998)); *Bacillus* sp. PHYT (SWISSPROT 066037, FEMS Microbiol. Lett. 162: 185-191 (1998); *Bacillus subtilis* PHYT_ (SWISSPROT P42094, J. Bacteriol. 177:6263-6275 (1995)); the phytase disclosed in AU 724094, or WO 97/33976;

vi) *Escherichia coli* (e.g. U.S. Pat. No. 6,110,719);

vii) *Citrobacter*, such as *Citrobacter freundii* (disclosed in WO 2006/038062, WO 2006/038128, or with the sequence of UniProt Q676V7), *Citrobacter braakii* (disclosed in WO 2004/085638 (Geneseqp ADU50737), and WO 2006/037328), and *Citrobacter amalonaticus* or *Citrobacter gillenii* (disclosed in WO 2006/037327);

viii) Other bacterial phytases such as the phytase from *Buttiauxella* (disclosed in WO 2006/043178);

ix) Yeast phytases, e.g. from *Schwanniomyces occidentalis* (e.g. disclosed in U.S. Pat. No. 5,830,732); as well as x) a phytase having an amino acid sequence of at least 75% identity to a mature amino acid sequence of any one of the phytases of (i)-(ix);

xi) a variant of the phytase of (i)-(ix) comprising a substitution, deletion, and/or insertion of one or more amino acids;

xii) an allelic variant of the phytase of (i)-(ix);

xiii) a fragment of the phytase of (i)-(ix) that retains phytase activity; or xiv) a synthetic polypeptide designed on the basis of (i)-(ix) and having phytase activity.

Preferred examples of phytase variants are disclosed in e.g., WO 99/49022, WO 99/48380, WO 00/43503, EP 0897010, EP 0897985, WO 2003/66847, as well as in the above-mentioned WO 2006/038063, WO 2006/038128, and WO 2006/43178).

Examples of commercially available proteases (peptidases) include Kannase™ Everlase™, Esperase™, Alcalase™, Neutrase™, Durazym™, Savinase™, Ovozyme™ Pyrase™, Pancreatic Trypsin NOVO (PTN), Bio-Feed™ Pro and Clear-Lens™ Pro (all available from Novozymes NS, Bagsvaerd, Denmark). Other preferred proteases include those described in WO 01/58275 and WO 01/58276.

Other commercially available proteases include Ronozyme™ Pro, Maxatase™ Maxacal™, Maxapem™, Opticlean™, Propease™, Purafect™, and Purafect Ox™ (available from Genencor International Inc., Gist-Brocades, BASF, or DSM Nutritional Products), Cibenza from Novus, or Avizyme from BioResouces International.

Examples of commercially available lipases include Lipex™, Lipoprime™, Lipopan™ Lipolase™, Lipolase™, Ultra, Lipozyme™, Palatase™, Resinase™, Novozym™, 435 and Lecitase™ (all available from Novozymes NS).

Other commercially available lipases include Lumafast™ (*Pseudomonas mendocina* lipase from Genencor International Inc.); Lipomax™ (*Ps. pseudoalcaligenes* lipase from Gist-Brocades/Genencor Int. Inc.; and *Bacillus* sp. lipase from Solvay enzymes. Further lipases are available from other suppliers.

Examples of commercially available carbohydrases include Alpha-Gal™, Bio-Feed™ Alpha, Bio-Feed™ Beta, Bio-Feed™ Plus, Bio-Feed™ Wheat, Bio-Feed™ Z, Novozyme™ 188, Carezyme™, Celluclast™, Cellusoft™, Celluzyme™, Ceremyl™, Citrozym™ Denimax™, Dezyme™, Dextrozyme™, Duramyl™, Energex™, Finizym™, Fungamyl™ Gamanase™, Glucanex™, Lactozym™, Liquezyme™, Maltogenase™, Natalase™ Pentopan™, Pectinex™, Promozyme™, Pulpzyme™, Novamyl™, Termamyl™, AMG™ (Amyloglucosidase Novo), Maltogenase™, Sweetzyme™ and Aquazym™ (all available from Novozymes NS). Further carbohydrases are available from other suppliers, such as the Roxazyme™, and Ronozyme™, product series (DSM Nutritional Products), the Avizyme™ Porzyme™, and Grindazyme™ product series (Danisco, Finnfeeds), and Natugrain™ (BASF), Purastar™, and Purastar™ OxAm (Genencor).

Other commercially available enzymes include Mannaway™, Pectaway™ Stainzyme™ and Renozyme™.

In a particular embodiment of the compositions described herein, the feed enzyme is selected from the group consisting of endoglucanases, endo-1,3(4)-beta-glucanases, proteases, phytases, galactanases, mannanases, dextranases and alpha-galactosidase, and reference is made to WO 2003/062409 which is hereby incorporated by reference.

Particular suitable feed enzymes include: amylases, phosphotases, such as phytases, and/or acid phosphatases; carbohydrases, such as amylytic enzymes and/or plant cell wall degrading enzymes including cellulases such as β-glucanases and/or hemicellulases such as xylanases or galactanases; proteases or peptidases such as lysozyme; galatosidases, pectinases, esterases, lipases, in particular phospholipases such as the mammalian pancreatic phospholipases A2 and glucose oxidase. In particular the feed enzymes have a neutral and/or acidic pH optimum. In a particular embodiment of the compositions described herein the feed enzyme is selected from the group consisting of amylases, phosphotases, phytases, cellulases, β-glucanases, hemicellulases, proteases, peptidases, galatosidases, pectinases, esterases, lipases and glucose oxidase.

In a particular embodiment of the compositions described herein the enzyme is selected from the group consisting of amylases, proteases, beta-glucanases, phytases, xylanases, phospholipases and glucose oxidases.

Animal Feed

In certain embodiments the compositions described herein are suitable for use in animal feed(s). The characteristics of the compositions described herein allow its use as a component which is well suited for inclusion with an animal feed. In particular embodiments, the compositions described herein are mixed with an animal feed ingredient and/or animal feed(s) and referred to as a mash feed. In certain embodiments, the mash feed is subsequently pelletized.

The animal feed may comprise any ingredient suitable for intake by aquatic animals, e.g., comprising sources of protein, lipids, carbohydrates, salts, minerals and vitamins. The animal feed ingredients may be selected, and mixed in any proportions, suitable to meet the nutritional needs of the aquatic animals to be fed with the feed and/or to keep the raw material cost of the feed within desired limits and/or to achieve other desired properties of the feed. Non-limiting examples of animal feed ingredients may include one or more of the following materials: plant derived products, such as seeds, grains, leaves, roots, tubers, flowers, pods, husks, oil, soybean meal, soy protein isolate, potato protein powder, wheat, barley, corn, soybean oil, and corn gluten meal; animal derived products, such as fish meal, fish oil, milk powder, skim milk powder, bone extract, meat extract, blood extract, and the like; additives, such as minerals, vitamins, aroma compounds, and feed enhancing enzymes.

In particular embodiments, the animal feed may comprise 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

In another embodiment, the animal feed may optionally comprise one or more suitable animal feed additives. Non-limiting examples of suitable animal feed additives include enzyme inhibitors, fat-soluble vitamins, water soluble vitamins, trace minerals, macro minerals, and combinations thereof.

In another embodiment, the animal feed may further optionally comprise one or more feed-additive ingredients. Non-limiting examples of feed-additive ingredients include colouring agents, aroma compounds, stabilisers, anti-microbial peptides (non-limiting examples of anti-microbial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity), anti-fungal polypeptides (AFP's) (non-limiting examples include the *Aspergillus giganteus*, and *Aspergillus niger* peptides, as well as variants and fragments thereof which retain antifungal activity, as disclosed in WO 94/01459 and PCT/DK02/00289), and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

In still another embodiment, the animal feed may still further optionally include one or more fat- and water soluble vitamins, trace minerals and macro minerals. Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium, zinc, etc.

Non-limiting examples of macro minerals include calcium, magnesium, potassium, sodium, etc.

Methods

In another aspect, methods for improving the health of an aquatic animal are described herein. In a particular embodiment, the method comprises the step of administering to an aquatic animal one or more bacterial strains, wherein the one or more bacterial strain are from the genus *Bacillus*. In a more particular embodiment, the method comprises the step of administering to an aquatic animal one or more bacterial strains selected from the group consisting of *Bacillus amyloliquifaciens, Bacillus subtilis, Bacillus pumilus, Bacillus polymyxa, Bacillus licheniformis, Bacillus megaterium, Bacillus coagulans, Bacillus circulans*, and combinations thereof.

In an even more particular embodiment, the method comprises the step of administering to an aquatic animal one or more bacterial strains, wherein the one or more bacterial strains are selected from the group consisting of:
the strain having the deposit accession number NRRL B-50136;
the strain having the deposit accession number NRRL B-50622;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50606;
the strain having the deposit accession number PTA-7547;
the strain having the deposit accession number NRRL B-50304;
the strain having the deposit accession number NRRL B-50349, and combinations thereof.

In still an even more particular embodiment, the method comprises the step of administering to an aquatic animal one or more bacterial strains such as at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, up to and including all of the above strains.

In another embodiment, the method comprises the step of administering to an aquatic animal the strain having the deposit accession number NRRL B-50136. In yet another embodiment, the method comprises the step of administering to an aquatic animal the strain having the deposit accession number NRRL B-50622. In still another embodiment, the method comprises the step of administering to an aquatic animal the strain having the deposit accession number NRRL B-50605. In yet another embodiment, the method comprises the step of administering to an aquatic animal the strain having the deposit accession number NRRL B-50016. In still a further embodiment, the method comprises the step of administering to an aquatic animal the strain having the deposit accession number NRRL B-50017. In still a further embodiment, the method comprises the step of administering to an aquatic animal the strain having the deposit accession number NRRL B-50141. In another embodiment, the method comprises the step of administering to an aquatic animal the strain having the deposit accession number NRRL B-50607. In still another embodiment, the method comprises the step administering to an aquatic animal the strain having the deposit accession number NRRL B-50151. In still yet another embodiment, the method comprises the step of administering to an aquatic animal the strain having the deposit accession number NRRL B-50606. In yet another embodiment, the method comprises the step of administering to an aquatic animal the strain having the deposit accession number PTA-7547. In still yet another embodiment, the method comprises the step of administering to an aquatic animal the strain having the deposit accession number NRRL B-50304. In a further embodiment, the method comprises the step of administering to an aquatic animal the strain having the deposit accession number NRRL B-50349.

In still yet another embodiment of the method, the one or more bacterial strains are present in the form of a stable spore. In still a further embodiment of the method, the stable spore will germinate in the gut of the aquatic animal.

In a particular embodiment, the method comprises administering to an aquatic animal one or more bacterial strains described herein, wherein the bacterial count of the one or more bacterial strains is between $1\times10^2$ and $1\times10^{12}$ CFU/g of the composition, particularly $1\times10^4$ and $1\times10^9$ CFU/g of the composition, and more particularly $1\times10^5$ and $5\times10^8$ CFU/g of the composition. In a more particular embodiment the bacterial count of the one or more bacterial strains described herein is between $1\times10^6$ and $1\times10^8$ CFU/g of the composition.

In another aspect, the method comprises the step of contacting the gut of an aquatic animal with one or more bacterial strains of *Bacillus*. In a more particular embodiment, the method comprises the step of contacting the gut of an aquatic animal with one or more bacterial strains selected from the group consisting of *Bacillus amyloliquifaciens, Bacillus subtilis, Bacillus pumilus, Bacillus polymyxa, Bacillus licheniformis, Bacillus megaterium, Bacillus coagulans, Bacillus circulans*, and combinations thereof.

In an even more particular embodiment, the method comprises the step of contacting the gut of an aquatic animal with one or more bacterial strains wherein the one or more bacterial strains are selected from the group consisting of:
the strain having the deposit accession number NRRL B-50136;
the strain having the deposit accession number NRRL B-50622;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;

the strain having the deposit accession number NRRL B-50151;

the strain having the deposit accession number NRRL B-50606;

the strain having the deposit accession number PTA-7547;

the strain having the deposit accession number NRRL B-50304;

the strain having the deposit accession number NRRL B-50349, and combinations thereof.

In still an even more particular embodiment, the method comprises the step of contacting the gut of an aquatic animal with one or more bacterial strains such as at least two of the above strains, at least three of the above strains, at least four of the above strains, at least five of the above strains, at least six of the above strains, at least seven of the above strains, at least eight of the above strains, at least nine of the above strains, at least ten of the above strains, at least eleven of the above strains, at least twelve of the above strains, up to an including all of the above strains.

In another embodiment, the method comprises the step of contacting the gut of an aquatic animal with the strain having the deposit accession number NRRL B-50136. In yet another embodiment, the method comprises the step of contacting the gut of an aquatic animal with the strain having the deposit accession number NRRL B-50622. In still another embodiment, the method comprises the step of contacting the gut of an aquatic animal with the strain having the deposit accession number NRRL B-50605. In yet another embodiment, the method comprises the step of contacting the gut of an aquatic animal with the strain having the deposit accession number NRRL B-50016. In still a further embodiment, the method comprises the step of contacting the gut of an aquatic animal with the strain having the deposit accession number NRRL B-50017. In still a further embodiment, the method comprises the step of contacting the gut of an aquatic animal with the strain having the deposit accession number NRRL B-50141. In another embodiment, the method comprises the step of contacting the gut of an aquatic animal with the strain having the deposit accession number NRRL B-50607. In still another embodiment, the method comprises the step of contacting the gut of an aquatic animal with the strain having the deposit accession number NRRL B-50151. In still yet another embodiment, the method comprises the step of contacting the gut of an aquatic animal with the strain having the deposit accession number NRRL B-50606. In yet another embodiment, the method comprises the step of contacting the gut of an aquatic animal with the strain having the deposit accession number PTA-7547. In still yet another embodiment, the method comprises the step of contacting the gut of an aquatic animal with the strain having the deposit accession number NRRL B-50304. In a further embodiment, the method comprises the step of contacting the gut of an aquatic animal with the strain having the deposit accession number NRRL B-50349.

In still yet another embodiment of the method, the one or more bacterial strains are present in the form of a stable spore. In still a further embodiment of the method, the stable spore will germinate in the gut of the aquatic animal.

In still another embodiment, the method comprises contacting the gut of an aquatic animal with one or more bacterial strains described herein, wherein the bacterial count of the one or more bacterial strains is between $1\times10^2$ and $1\times10^{12}$ CFU/g of the composition, particularly $1\times10^4$ and $1\times10^9$ CFU/g of the composition, and more particularly $1\times10^5$ and $5\times10^8$ CFU/g of the composition. In a more particular embodiment the bacterial count of the one or more bacterial strains described herein is between $1\times10^6$ and $1\times10^8$ CFU/g of the composition.

In a particular embodiment, the method comprises the step of contacting the gut of an aquatic animal with one or more of the bacterial strains described herein the one or more bacterial strains improve the health of the aquatic animal by increasing the weight or the aquatic animal.

In still another embodiment, the one or more bacterial strains improve the health of the aquatic animal by enhancing the immune system and/or immune response of the aquatic animal.

In yet another embodiment, the one or more bacterial strains improve the health of the aquatic animal by improving the overall health of the gut of the aquatic animal. Non-limiting examples of improved gut health include reducing gut inflammation, increasing the length and/or surface area of intestinal villi, increasing intestinal crypt depth, improving nutrient absorption by the gut, maintaining and/or improving healthy gut microflora, or combinations thereof.

In still yet another embodiment the one or more bacterial strains improve the health of the aquatic animal by controlling pathogenic microorganisms. In a particular embodiment, the one or more bacterial strains improve the health of the aquatic animal by controlling pathogenic microorganisms in the gut of the aquatic animal.

In one embodiment the one or more bacterial strains control pathogenic microorganisms belonging to the genus *Aeromonas*. In a more particular embodiment, the one or more bacterial strains control pathogenic microorganisms selected from the group consisting of *Aeromonas hydrophila, Aeromonas punctata, Aeromonas salmoncida, Aeromonas veronii*, or combinations thereof.

In a further embodiment, the one or more bacterial strains control pathogenic microorganisms belonging to the genus *Vibrio*. In a more particular embodiment, the one or more bacterial strains control pathogenic microorganisms selected from the group consisting of *Vibrio fischeri, Vibrio vulnificus, Vibrio fluvialis, Vibrio parahaemolyticus, Vibrio alginolyticus, Vibrio mimicus, Vibrio cholera, Vibrio harveyi*, or combinations thereof.

In yet still another embodiment, the one or more bacterial strains control pathogenic microorganisms belonging to the genus *Serratia*. In a more particular embodiment, the one or more bacterial strains control pathogenic microorganisms selected from the group consisting of *Serratia entomophila, Serratia ficaria, Serratia fonticola, Serratia grimesii, Serratia liquefaciens, Serratia marcescens, Serratia odorifera, Serratia plymuthica, Serratia proteamaculans, Serratia quinivorans, Serratia rubidaea, Serratia symbiotica*, or combinations thereof.

In still yet a further embodiment, the one or more bacterial strains control pathogenic microorganisms belonging to the genera *Aeromonas, Vibrio, Serratia* and combinations thereof. In a more particular embodiment, the one or more bacterial strains control pathogenic microorganisms selected from the group consisting of *Aeromonas hydrophila, Aeromonas punctata, Aeromonas salmoncida, Aeromonas veronii, Vibrio fischeri, Vibrio vulnificus, Vibrio fluvialis, Vibrio parahaemolyticus, Vibrio alginolyticus, Vibrio mimicus, Vibrio cholera, Vibrio harveyi, Serratia entomophila, Serratia ficaria, Serratia fonticola, Serratia grimesii, Serratia liquefaciens, Serratia marcescens, Serratia odorifera, Serratia plymuthica, Serratia proteamaculans, Serratia quinivorans, Serratia rubidaea, Serratia symbiotica*, or combinations thereof.

In a particular embodiment, the aquatic animals is a fish (e.g., catfish, tilapia, trout, salmon, perch, bass, tuna, wahoo, tuna, swordfish, marlin, grouper, sturgeon, snapper, eel and walleye, sharks, rays, and skates), a crustacean (e.g., crabs, lobsters, crayfish, shrimp, krill, and prawn) a mollusk (e.g., snails, slugs, conch, squid, octopus, cuttlefish, clams, oysters, scallops, and mussels), and combinations thereof. In an even more particular embodiment, the aquatic animal is a fish, a shrimp, a lobster, an eel, a crayfish, a prawn, an oyster, a mussel, a cockle, or a combination thereof. In an even more particular embodiment, the aquatic animal is a catfish, a tilapia, a shrimp or combinations thereof.

Manufacturing Processes

In still another embodiment, methods described herein comprise administering to an aquatic animal and/or contacting the gut of an aquatic animal with a composition described herein. In a particular embodiment, the composition is an ingredient in an animal feed (i.e., a mash feed) as described herein.

In an even more particular embodiment, the feed mash is pelleted. Pelleting processes are known in the art. In a particular embodiment, the pellets are manufactured through a pelleting process. In another embodiment the pellets are manufactured through an extrusion process.

In an embodiment, the feed mixture (mash feed) may be prepared by mixing the composition comprising the one or more bacterial strains with desired feed components. In a particular embodiment the mash feed may be conditioned or unconditioned.

In one embodiment the mash feed is conditioned prior to the pelleting process. In a particular embodiment, the mash feed is led to a conditioner e.g., a cascade mixer with steam injection. The feed is in the conditioner heated up to a specified temperature, 60-120° C., e.g. 60° C., 70° C., 80° C., 90° C., 100° C., 105° C., 110° C., 115° C., and 120° C. by injecting steam, measured at the outlet of the conditioner. The residence time can be variable from seconds to minutes and even hours. Such as 5 seconds, 10 seconds, 15 seconds, 30 seconds, 1 minute, 2 minutes, 5 minutes, 10 minutes, 15 minutes, 30 minutes, 1 hour, 2 hours, 3 hours, 4, hours, 5 hours, 6 hours, 7 hours, 8, hours, 9, hours, 10 hours, 11 hours, 12 hours, and up to 24 hours and beyond. In a particular embodiment, the process temperature during steam treatment is at least 60° C. In a more particular embodiment, the process temperature during steam treatment is at least 70° C. In an even more particular embodiment, the process temperature during steam treatment is at least 80° C. In a most particular embodiment, the process temperature during steam treatment is at least 90° C.

In another embodiment, the pelleting process is an extrusion process. Typical, extrusion processes for manufacturing feed pellets are known to those skilled in the art. Extrusion or pelletized products, wherein the feed mixture (mash feed) is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the mash feed. (Michael S. Showell (editor); Powdered detergents; Surfactant Science Series; 1998; vol. 71; page 140-142; Marcel Dekker).

In a particular embodiment, the mash feed is led to an extruder to form pellets of variable length from the extrudate. The extrusion apparatus may be any screw-type extruder known in the art. In a particular embodiment, the extruder is a double screwed extruder, e.g., a Werner & Pfleiderer Type continua 37" extruder. Extrusion parameters (e.g., capacity, screw speed, die diameter, drying temperatures, drying time, etc.) are dependent upon the particular extrusion process and/or extrusion apparatuses employed.

In an embodiment, the screw speed of the extruder is 1-1,000 RPM. In a more particular embodiment, the screw speed of the extruder is 100 RPM. In an even more particular embodiment, the screw speed of the extruder is 150 RPM. In yet an even more particular embodiment, the screw speed of the extruder is 200 RPM. In still an even more particular embodiment, the screw speed of the extruder is 250 RPM. In still yet an even more particular embodiment, the screw speed of the extruder is 300 RPM.

In an embodiment, the die diameter is 0.5 mm-5.0 mm. In a more particular embodiment, the die diameter is 0.5 mm. In an even more particular embodiment, the die diameter is 1.0 mm. In yet an even more particular embodiment, the die diameter is 1.5 mm. In a most particular embodiment, the die diameter is 2.0 mm.

The pellets are placed then dried for a specified time e.g., at least 15 minutes, preferably 20 minutes, at temperatures of 60-100° C., preferably 90-100° C., more preferably 90° C., even more preferably 95° C., even still more preferably 100° C.

EXAMPLES

The following examples are provided for illustrative purposes and are not intended to limit the scope of the invention as claimed herein. Any variations in the exemplified examples which occur to the skilled artisan are intended to fall within the scope of the present invention.

Materials & Methods

Chemicals used as buffers and reagents were commercial products of at least reagent grade.

Nutrient Broth:
   3.0 g/L Beef Extract;
   1.5 g/L Peptone

Standard Methods agar plates (SMA plates) (Smith River Biologicals, Ferrum, VA cat #11-00450).

Feed/Meal Formulation:

Feed was produced using the following ingredients and was mixed to make the meal homogenous:
   74% w/v grind corn;
   20.7% w/v toasted soy grits;
   5.0% w/v soy oil;
   0.3% w/v Solivit Mikro 106 premix.

Bacterial Strains:

| | Strain |
|---|---|
| Bacillus subtilis | NRRL B-50136; ATCC 55406 (SB3086) |
| Bacillus subtilis | PTA-7547 |
| Bacillus amyloliquefaciens | NRRL B-50349 |
| Bacillus amyloliquefaciens | NRRL B-50606 |
| Bacillus amyloliquefaciens | NRRL B-50151 |
| Bacillus amyloliquefaciens | NRRL B-50141 |
| Bacillus pumilus | NRRL B-50016 |
| Bacillus subtilis | NRRL B-50622 |
| Serratia rubidaea | (ATCC 27593) |
| Vibrio harveyi | (ATCC 25919) |
| Vibrio alginolyticus | (ATCC 17749) |
| Vibrio fisheri | (MJ-1): wild-type strain |
| Aeromonas hydrophila | (ATCC 7966) |

Example 1

In-Vitro Inhibition Potential

Competitive inhibition by a series of *Bacillus* candidate strains was assessed against a series of targeted pathogenic bacterial strains, including *Serratia rubidaea, Vibrio harveyei, Vibrio fischeri, Vibrio alginolyticus*, and *Aeromonas hydrophila*. Selected *Bacillus* strains were quantitatively assessed by their ability to inhibit the growth of a "lawn" of the target bacterial pathogen (as noted in Table 1) grown on a Petri plate. This is best quantified by using a defined "well" (hole) cut in the agar, into which is placed a defined amount of active culture of the test *Bacillus* strain.

Diffusion assays were performed where the test strain *Bacillus* candidates were grown in a Nutrient Broth which was autoclaved and cooled prior to strain inoculation. For tests involving inhibition of *Vibrio* species, the Nutrient Broth was supplemented with 1.5% (w/v) NaCl. *Bacillus* strains were grown on the Nutrient Broth for 18-24 hours to a density of approximately $10^7$ to $10^8$ CFU/ml. Target pathogens were similarly grown, streaked to form a lawn on the surface of Standard Methods Agar plates (SMA plates; Smith River Biologicals, Ferrum, VA). Four 5 mm holes were bored into the agar with a sterile stainless steel tube. 50 μl of each *Bacillus* liquid culture was delivered into the holes (1 strain per hole) and the plate was subsequently incubated for 18 to 48 hours at 35° C., agar side down. The inhibited target strain lawn in proximity to a hole was scored as positive biocontrol for the *Bacillus* candidate. The zone of inhibition, or the well diffusion (WD) was measured in millimeters (mm) to allow semi-quantitative assessment of control, with discernible inhibition >1 mm (beyond the 5 mm hole itself) was scored as a positive.

The results of this comparative inhibition are provided in Table 1.

TABLE 1

Relative Zone of Inhibition Assessment of Disease-Control Strains against Targeted Pathogens.

| Strain | WD against *Serratia rubidaea* (mm) | WD against *Vibrio harveyi* (mm) | WD against *Vibrio alginolyticus* (mm) | WD against *Aeromonas hydrophila* (mm) |
|---|---|---|---|---|
| NRRL B-50136 | 0 | 16.14 | 12 | 16 |
| PTA-7547 | 27.9 | 11 | 19 | 16 |
| NRRL B-50349 | 23.7 | 9 | 7 | 11 |
| NRRL B-50606 | 15.7 | 14 | 13 | 19 |
| NRRL B-50151 | 0 | 10 | 14 | 12.5 |
| NRRL B-50141 | | 9 | 7 | 12 |
| NRRL B-50016 | | 10 | 10 | 12.6 |
| NRRL B-50622 | | | | |

Example 2

Quorum Sensing Inhibition

*Vibrio fischeri* (MJ-1) was used as the indicator bacterium as its pigmentation is dependent on intact quorum sensing pathway. The higher the QSI effect on *V. fischeri*, the less fluorescence is observed. Quorum sensing compounds allow bacteria to "communicate" and affect phenotypes such as pigmentation, motility, pathogenicity, and *Vibrio* establishment in shrimp gills or the gut. Thus quorum sensing inhibition is a mode of action for such as *Vibrio* establishment in the gut.

*Bacillus* candidates and the indicator bacterium, *Vibrio fischeri* (MJ-1), were grown according to the methods of Example 1. Results are provided in Table 2. Zones of inhibited pigmentation, but not total cell growth inhibition, were scored positive for QSI and measured across their full diameter for semi-quantitative results. Total growth inhibition of *V. fischeri* was indicated as "VC", for vibriocidal.

TABLE 2

Relative Zone of QSI.

| Strain | WD against *Vibrio fischeri* (mm)-QSI indicator | Vibriocidal (VC) or QSI (against *V. fischeri*) |
|---|---|---|
| NRRL B-50136 | 14 | VC |
| PTA-7547 | 15 | QSI |
| NRRL B-50349 | 11.6 | QSI |
| NRRL B-50606 | 17 | VC |
| NRRL B-50151 | 15 | QSI |

Example 3

Spore Survival in Extruded Fish Feed Pellets

For *Bacillus* strains to be effective in the aquatic feed itself, the inoculated spores must survive at effective levels during the pelletization process. Typically, the best fish feed value is obtained when the feed pellets are extruded through high-temperature (100° C. to 120° C.) nozzles prior to drying and subsequent feeding, while other animal feed types are sufficiently formed at 85-95° C.

An assessment was made of the survival potential for microbial spores during the standard fish food pelletization process. Commercial fish feed is generally prepared using a high-temperature extrusion process, where a feed mash is extruded through heated nozzles under defined temperature and pressure regimes. Trials were carried out using a Werner & Pfleiderer 37 screw-driven extruder, through a 2.7 mm dye nozzle with horizontal mixing, under temperatures described in Table 3.

Microbes were added as a dry spore concentrate to meal (see Materials and Methods) prior to extrusion using a horizontal mixer to achieve a target concentration of $1.0 \times 10^6$ CFU/g feed. Trials were carried out using meal fed at 18.9 kg/hr, water added at 4.7 kg/hr, extrusion output at 24.3 kg/hr, screw rate at 300 rpm, pressure at 36 bar, drying regime at 85° C. for 20 min, with final density of 450 g/L and moisture at 7.8% w/v. Results are provided in Table 3.

TABLE 3

Percent survival of Extrusion Pelletization Process.

| Strain | 23° C. | 85° C. | 95° C. | 100° C. | 110° C. | 120° C. |
|---|---|---|---|---|---|---|
| NRRL B-50606 | 100% | 95% | 100% | 53% | 30% | 0.6% |
| NRRL B-50136 | 100 | 98 | 100 | 63 | 30 | 0.8 |
| PTA-7547 | 100 | 69 | 31 | 0.8 | 0.2 | 0.05 |

ND: Not determined

A comparative evaluation of Bacterial spore survival and recovery from Fish Feed following a standard pelletization and high-temperature extrusion pelletization process was completed. Results indicate that two strains in the study, NRRL B-50606 and NRRL B-50136, are capable of significant survival (30%) up to 110° C. extrusion temperatures, and >50% survival at 100° C. extrusion.

Example 4

Ability of Spores to Enhance Fish Survival During Disease Challenge; Test-1

Striped catfish were obtained from a local hatchery, and transported, quarantined and maintained according standard husbandry practices. Apparently healthy animals were randomly allocated to the tanks, and acclimated for >1 week before initiation of the trial.

90 Striped Catfish per tank were grown from the initial 40 g size in four replicate 900 L tanks for each Treatment group and Control group. Fish were fed a standard balanced fish diet at 3% body weight per day in 2 feedings. The water temperature was 28° C.±2° C., light period was ambient and 12:12 hr artificial light. The fish were fed Test Diets of specific spore-containing feed or feed alone (Control) for 2 weeks prior to a 2-week challenge period with the pathogen *Edwardsiella ictaluri*. The specific spore-containing feed used in the Challenge studies was prepared as described in Example 3, but with extrusion temperature at 95° C. and with a final total bacterial spore target of 1×10e7 CFU/g feed. For this study only one bacterial type was tested in each feed batch.

During the challenge, fish (n=25) were transferred to 100 L tanks for a bath challenge with *E. ictaluri*. Fish were immersed for 30 min in static, aerated aquaria at a dose of 10e6 CFU/ml to target 60-70% mortality in the Control group. The control and test diets were offered throughout the challenge phase. Mortality was monitored at least twice daily before feeding for a minimum of 14 days, and ended when no mortalities occurred for more than 2 consecutive days in all the tanks. Any moribund or dead fish were removed and checked for gross external and internal clinical signs of disease and the kidney sampled for bacterial recovery.

The results are presented in Table 4 as Relative Percent Survival (RPS) where:

RPS (%)=1−(mortality in treated tanks/mortality in control tanks)×100

For statistical analysis, data was assessed using one-way analysis of variance (ANOVA), and multiple comparisons among treatment means were made with the Least Significant Difference (LSD) method using the procedures of SAS®. Survival analysis was performed on the challenge data as follows. Product-limit survival curves were developed for each treatment and compared using the non-parametric Wilcoxon test. Results were considered statistically significant at $P<0.05$.

TABLE 4

Relative Survival of Pangasius Catfish Test-1

| Bacteria in Feed | Relative % Survival | Statistical Grouping |
| --- | --- | --- |
| Control (no added spores) | 0 | A |
| NRRL B-50136 (SB3086) | 59.6 | B |
| NRRL B-50349 (SB3615) | 61.5 | B |
| PTA-7547 (SB3295) | 57.7 | B |

All three bacterial strains added to the feed provided significant protection and produced increased relative survival for the fish being fed each of the augmented bacterial direct-fed treatments.

Example 5

Ability of Multiple Spores to Enhance Fish Survival During Disease Challenge; Test-2

As described in Example 4, extruded fish feed pellets containing the spores of the *Bacillus* strains were added to the extruded pellet feeds in single and certain dual-strain blends. As before, these feeds were fed to Striped Catfish Pangasianodon hypophthalmus during infection by the bacterial pathogen *Edwardsiella ictaluri* in multiple test aquarium tanks. In this study, a blend of two bacterial spore types was also used. In these dual treatments, equal amounts of each bacterial spore type were added to a final total concentration of 1×10e7 CFU/g.

The same test design and statistical evaluations were applied as used in Example 4. Results are provided in Table 5.

TABLE 5

Relative Survival of Pangasius Catfish Test-2 with individual and dual blends of spore in the treated feed.

| Bacteria in Feed | Relative % Survival | Statistical Grouping |
| --- | --- | --- |
| Control (no added spores) | 0 | A |
| NRRL B-50349 | 27.8 | B |
| PTA-7547 | 31.6 | B |
| NRRL B-50136 + PTA-7547 | 36.7 | Cb |
| NRRL B-50136 | 38.0 | Cb |
| NRRL B-50136 + NRRL B-50349 | 51.9 | C |

Results confirm that each strain and the combination of strains are significantly better than the non-inoculated Control. The combination of NRRL B-50136 N and RRL B-50349 are especially effective in reducing the effect of the pathogen on fish survival. It should be noted that the absolute level of protection is subjected to numerous environmental conditions and relative robustness of the fish used in the specific studies. Therefore, the relative performance of the Treated fish within the specific test study compared with the identical non-treated Control fish is of primary importance.

Example 6

Enhancement of Intestinal Tissues and Increase in Muscle Mass Ratio

A grow-out trial of Tilapia in multiple fish tanks demonstrated the ability of the *Bacillus* bacteria to positively affect the health of the intestinal tissues, particularly the microvilli lining the gut surface. In addition, measurement of the muscle mass ratio (MR) on treated fish was found to significantly increase in fish fed the *Bacillus*.

The 14 week experimental trial was performed in two identical and independent recirculating aquaculture systems each equipped with twelve 210 liter round polyethylene tanks, a bubble bead filter for mechanical filtration, a fluidized-bed bioreactor for biological wastewater treatment, a UV disinfection unit, immersion titanium heaters, and distributed diffusion aeration. In one system the fish were fed treatment diet (with probiotic strain NRRL B-50136 on the feed). On the other system, fish were fed the control diet (no additional microbes to the same feed).

Tanks were scrubbed for biofouling once per week, bead filters backwashed three times per week, and fresh water supplemented for water loss during backwashes. Systems were heated for a target temperature of 29° C. Throughout the duration of the trial, systems were exposed to a photoperiod of 12:12 light/dark cycle. Alkalinity was maintained at levels sufficient for effective nitrification and suitable pH for tilapia.

Water quality parameters monitored included alkalinity, dissolved oxygen, nitrate, nitrite, pH, temperature, and total ammonia. Samples were tested for each system on alternating days and results of the various water quality parameters demonstrated no significant difference between Bacterial Treatment and Control group. Alkalinity was determined using HACH® method 8203 (Hach Company P.O. Box 389 Loveland, Colorado), using a Digital Titrator. Dissolved oxygen (DO), salinity, and temperature were determined with an YSI 85 probe. A VWR® Symphony™ SB70P pH meter was used to determine pH. Nitrate-N, Nitrite-N, and total ammonia-N (TAN) were measured in accordance with HACH® spectrophotometric methods 8507, 8039, and 8038, respectively, using a HACH® DR/2800™ spectrophotometer. Throughout the duration of the trial, water quality parameters were maintained within ranges satisfactory for tilapia growth.

The tilapia (*Oreochromis niloticus*) used in this trial were acquired from a commercial farm and transported to the testing site. Fish were separated at random and distributed evenly between two 12-tank systems at 13 fish per tank, for an initial stocking total of 156 fish per group. Upon receipt, fish weighed 75±2.1 grams, and following an acclimation period, yielded 119.1±0.1 g fish in the treatment group, and 119.3±0.1 g fish in the control group. Within this acclimation period, water temperatures were held at ~26° C. and fed a control diet twice daily for maintenance. When all features of the trial were in place, and the fish appeared healthy, the trial commenced.

Fish were weighed weekly to track growth and for feed management. At Day 0, three fish were sampled from each group for biometrics at random from three different tanks within each group. The remaining tanks were reduced in number to begin the trial with twelve fish per tank, for a group N=144.

Feed was formulated and manufactured by Wenger Feeds (Sabetha, KS) in a standard formulation for Tilapia growth. The Control diet (used throughout the 14-week study) was surface coated with oil only, for a measured total lipid content of 1.5%. The preparation of the Treatment diet (with Probiotic strain NRRL B-50136) was prepared by standard surface coating with lipid-probiotic aggregate. After preparation, the final lipid content was 1.5% w/w.

Feed was kept in a temperature-controlled room, elevated above the floor. Fish were fed once every 45 minutes over an 8-hour daily period at varying rates proportional to body weight and consumption. Feeding rates were initialized at 3.0% of body weight and were reduced gradually to 1.4% of body weight near the end of the trial.

This study used the R statistical software program to evaluate the data collected. Descriptive statistical analysis was performed to present the data and Student's t-test was used to determine significant differences (P<0.05).

Fish were randomly sampled from a random tank selection to track biometric parameters and diagnostic health at five time points: Day 0, at the end of Week 1, Week 2, Week 3, Week 6, and Week 14 at the end of the trial. Tanks that had been previously sampled were not included in the random selection. Three fish from each group were sampled for the first four time points, and nine from each group at the trial end. Blood samples were drawn from each fish to track packed cell volumes (PCV) by hematocrit centrifugation and total plasma protein content estimations by refractometry. Fish were then euthanized in accordance with IACUC guidance, and necropsies were performed, where liver, viscera, and fillets were weighed to index against total body weight to yield Hepatosomatic Index values (HSI), Visceral-Somatic Index values (VSI), and Muscle Mass Ratio (MR; also referred to as Filet Weight), respectively; and general fish condition is presented as Fulton's Condition Factor (K). Final biometric indices and measurements are presented in Table 6. Between the two groups, only PCV values and Muscle Ratio were found to be significantly different (P=0.02 and P=0.04 respectively); where PCV values were significantly higher in the Control Group, and Muscle Ratios were greater in the Treatment Group.

TABLE 6

Summary of final biometric results (n = 9)

| Biometrics | K [g/cm$^3$] | PCV [%] | Total plasma protein [g/100 mL] | HIS | VSI | MR [%] |
|---|---|---|---|---|---|---|
| Treatment | 3.75 | 23.8$^a$ | 14.8 | 2.09 | 2.62 | 39.6$^a$ |
| Control | 3.70 | 26.3$^b$ | 15.2 | 2.07 | 2.77 | 35.6$^b$ |

Histological analysis of intestinal samples showed a significant visual difference in the microvilli density and length from the Treatment and Control groups (microvilli: microscopic cellular membrane protrusions that increase the surface area of cells, and are involved in a wide variety of functions). For this evaluation, six NRRL B-50136-Treated fish and six Control-treated fish were dissected and intestinal sections were embedded in 1% (w/v) Uranyl-acetate prior to standard Transmission Electron Microscopy. FIG. 1 shows the results and Table 7 summarizes this.

TABLE 7

Microvilli Length in Tilapia Intestinal Sections

| Intestinal Parameter | B-50136 Treated Tilapia | Control Tilapia |
|---|---|---|
| Microvilli length | 1.56 ± 0.051 µm | 1.22 ± 0.068 µm |
| % Increase | 28% (P < 0.05) | — |

The present invention is further defined by the following paragraphs:

1. A method for improving the well-being, general condition or health of an aquatic animal comprising administering to the aquatic animal an effective amount of one or more bacterial strains for improving the health of the aquatic animal, wherein the one or more bacterial strains are selected from the group consisting of:

the strain having the deposit accession number NRRL B-50136;
the strain having the deposit accession number NRRL B-50349;
the strain having the deposit accession number NRRL B-50606;
the strain having the deposit accession number NRRL B-50016;

the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50605;
the strain having the deposit accession number PTA-7547;
the strain having the deposit accession number NRRL B-50304;
the strain having the deposit accession number NRRL B-50622, and combinations thereof.

2. The method of paragraph 1, wherein the method comprises administering to the aquatic animal an effective amount of a bacterial strain having the strain having the deposit accession number NRRL B-50136.

3. The method of paragraph 1 or 2, wherein the method comprises administering to the aquatic animal an effective amount of a bacterial strain having the strain having the deposit accession number NRRL B-50622.

4. The method of any of paragraphs 1-3, wherein the method comprises administering to the aquatic animal an effective amount of a bacterial strain having the strain having the deposit accession number NRRL B-50605.

5. The method of any of paragraphs 1-4, wherein the method comprises administering to the aquatic animal an effective amount of a bacterial strain having the strain having the deposit accession number NRRL B-50016.

6. The method of any of paragraphs 1-5, wherein the method comprises administering to the aquatic animal an effective amount of a bacterial strain having the strain having the deposit accession number NRRL B-50017.

7. The method of any of paragraphs 1-6, wherein the method comprises administering to the aquatic animal an effective amount of a bacterial strain having the strain having the deposit accession number NRRL B-50141.

8. The method of any of paragraphs 1-7, wherein the method comprises administering to the aquatic animal an effective amount of a bacterial strain having the strain having the deposit accession number NRRL B-50607.

9. The method of any of paragraphs 1-8, wherein the method comprises administering to the aquatic animal an effective amount of a bacterial strain having the strain having the deposit accession number NRRL B-50151.

10. The method of any of paragraphs 1-9, wherein the method comprises administering to the aquatic animal an effective amount of a bacterial strain having the strain having the deposit accession number NRRL B-50606.

11. The method of any of paragraphs 1-10, wherein the method comprises administering to the aquatic animal an effective amount of a bacterial strain having the strain having the deposit accession number PTA-7547.

12. The method of any of paragraphs 1-11, wherein the method comprises administering to the aquatic animal an effective amount of a bacterial strain having the strain having the deposit accession number NRRL B-50304.

13. The method of any of paragraphs 1-12, wherein the method comprises administering to the aquatic animal an effective amount of a bacterial strain having the strain having the deposit accession number NRRL B-50349.

14. The method of any of paragraphs 1-13, wherein the one or more bacterial strains improve the health of the aquatic animal by increasing the weight of the aquatic animal.

15. The method of any of paragraph 1-14, wherein the one or more bacterial strains improve the health of the aquatic animal by reducing inflammation in the gut of the aquatic animal.

16. The method of any of paragraphs 1-15, wherein the one or more bacterial strains improve the health of the aquatic animal by increasing the surface area of the intestinal villi of the aquatic animal.

17. The method of any of paragraphs 1-16, wherein the one or more bacterial strains improve the health of the aquatic animal by increasing length of the intestinal villi of the aquatic animal.

18. The method of any of paragraphs 1-17, wherein the one or more bacterial strains maintain healthy gut microflora in the aquatic animal.

19. The method of any of paragraphs 1-18, wherein the one or more bacterial strains improve the health of the aquatic animal by controlling pathogenic microorganisms in the gut of the aquatic animal.

20. The method of paragraph 19, wherein the pathogenic microorganisms are of the genus *Vibrio*.

21. The method of paragraph 20, wherein the pathogenic microorganisms are selected from the group consisting of *Vibrio fischeri*, *Vibrio vulnificus*, *Vibrio fluvialis*, *Vibrio parahaemolyticus*, *Vibrio alginolyticus*, *Vibrio mimicus*, *Vibrio cholera*, *Vibrio harveyi*, and combinations thereof.

22. The method of paragraph 19, wherein the pathogenic microorganisms are of the genus *Aeromonas*.

23. The method of paragraph 22, wherein the pathogenic microorganisms are selected from the group consisting of *Aeromonas hydrophila*, *Aeromonas punctata*, *Aeromonas salmoncida*, *Aeromonas veronii*, and combinations thereof.

24. The method of paragraph 19, wherein the pathogenic microorganisms are of the genus *Serratia*.

25. The method of paragraph 24, wherein the pathogenic microorganisms are selected from the group consisting of *Serratia entomophila*, *Serratia ficaria*, *Serratia fonticola*, *Serratia grimesii*, *Serratia liquefaciens*, *Serratia marcescens*, *Serratia odorifera*, *Serratia plymuthica*, *Serratia proteamaculans*, *Serratia quinivorans*, *Serratia rubidaea*, *Serratia symbiotica*, and combinations thereof.

26. The method of any of paragraphs 1-25, wherein the aquatic animal is selected from the group consisting of fish, shrimp, lobster, eel, crayfish, bottom dwelling fish, finfish, prawns, oysters, mussels, cockles, mollusks, and combinations thereof.

27. The method of paragraph 26, wherein the aquatic animal is a shrimp.

28. The method of paragraph 26, wherein the aquatic animal is a fish.

29. The method of paragraph 26, wherein the aquatic animal is a catfish.

30. The method of paragraph 26, wherein the aquatic animal is a tilapia.

31. The method of any of the preceding paragraphs, wherein the step of administering to the aquatic animal an effective amount of one or more bacterial strains comprises contacting the gut of the aquatic animal with one or more bacterial strains.

32. The method of any of the preceding paragraphs, wherein the step of administering an effective amount of one or more bacterial strains comprises administering to the aquatic animal one or more bacterial strains in a spore form.

33. The method of paragraph 32, wherein the spore form of the one or more bacterial strains germinates in the gut of the aquatic animal.

34. The method of any of the preceding paragraphs, wherein the step of administering is repeated at least once.

35. A composition comprising an animal feed ingredient and one or more bacterial strains selected from the group consisting of:
the strain having the deposit accession number NRRL B-50136;
the strain having the deposit accession number NRRL B-50349;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50606;
the strain having the deposit accession number PTA-7547;
the strain having the deposit accession number NRRLB-50304;
the strain having the deposit accession number NRRL B-50622, and combinations thereof.

36. The composition of paragraph 35, wherein the composition is in the form of a pellet.

37. The composition of paragraph 35 or 36, wherein the composition is in the form of an extruded pellet.

38. The composition of any of paragraphs 35-37, wherein the one or more bacterial strains are in a spore form.

39. The composition of any of paragraphs 35-38, wherein the composition further comprises one or more enzymes.

40. The composition of any of paragraphs 35-39, wherein the bacterial count of one or more bacterial strains is $1 \times 10^2$ CFU/g of composition to $1 \times 10^{12}$ CFU/g of composition, preferably $1 \times 10^6$ CFU/g of composition to $1 \times 10^8$ CFU/g of composition.

41. An extruded composition comprising an animal feed ingredient and one or more bacterial strains, wherein the one or more bacterial strains are extrusion stable bacterial strains, the extrusion stable strains being:
a) stable strains when the strains are subjected to an extrusion process having a pressure of 1 bar to 40 bar;
b) stable strains when the strains are subjected to an extrusion process wherein the extrusion process temperatures are temperatures from 80° C. to 120° C.; and
c) strains that control one or more pathogenic microorganisms.

42. The composition of paragraph 41, wherein the strains are stable when the strains are subjected to an extrusion process wherein the extruder has a die diameter of 0.5 mm to 5.0 mm.

43. The composition of paragraph 41 to 42, wherein the extrusion stability of the bacterial strain(s) is determined by extrusion at 100° C. and 110° C. exhibiting 50% or more survival at 100° C. or 25% or more survival at 110° C. extrusion.

44. The composition of any of paragraphs 41-43 comprising an animal feed ingredient and one or more bacterial strains selected from the group consisting of:
the strain having the deposit accession number NRRL B-50136;
the strain having the deposit accession number NRRL B-50606;
the strain having the deposit accession number NRRL B-50622;
the strain having the deposit accession number NRRL B-50605;
the strain having the deposit accession number NRRL B-50016;
the strain having the deposit accession number NRRL B-50017;
the strain having the deposit accession number NRRL B-50141;
the strain having the deposit accession number NRRL B-50607;
the strain having the deposit accession number NRRL B-50151;
the strain having the deposit accession number NRRL B-50304; and
the strain having the deposit accession number NRRL B-50349, and combinations thereof.

45. The composition of paragraph 44, wherein the one or more bacterial strains are selected from:
the strain having the deposit accession number NRRL B-50136 and/or
the strain having the deposit accession number NRRL B-50606.

46. The composition of any of paragraphs 43-45, wherein the extrusion pressure is 35 to 37 bar.

47. The composition of any of paragraphs 41-46, wherein the bacterial count of one or more bacterial strains is $1 \times 10^2$ CFU/g of composition to $1 \times 10^{12}$ CFU/g of composition, preferably $1 \times 10^6$ CFU/g of composition to $1 \times 10^8$ CFU/g of composition.

It will be understood that the Specification and Examples are illustrative of the present embodiments and that other embodiments within the spirit and scope of the claimed embodiments will suggest themselves to those skilled in the art. Although this invention has been described in connection with specific forms and embodiments thereof, it would be appreciated that various modifications other than those discussed above may be resorted to without departing from the spirit or scope of the invention as defined in the appended claims. For example, equivalents may be substituted for those specifically described, and in certain cases, particular applications of steps may be reversed or interposed all without departing from the spirit or scope for the invention as described in the appended claims.

The invention claimed is:

1. A method comprising administering viable spores and/or cells of the *Bacillus subtilis* strain having the deposit accession number NRRL B-50136 to an aquatic animal, wherein the *Bacillus subtilis* strain having the deposit accession number NRRL B-50136 is administered to the aquatic animal in the form of an extruded pellet.

2. The method of claim 1, wherein the extruded pellet further comprises one or more enzymes.

3. The method of claim 1, wherein the aquatic animal is a fish.

4. The method of claim 1, wherein the aquatic animal is a trout.

5. The method of claim 1, wherein the aquatic animal is a catfish.

6. The method of claim 1, wherein the aquatic animal is a tilapia.

7. The method of claim 1, wherein the aquatic animal is a shrimp.

8. The method of claim 1, wherein said administering improves the health of the aquatic animal by increasing the weight of the aquatic animal.

9. The method of claim 1, wherein said administering improves the health of the aquatic animal by reducing inflammation in the gut of the aquatic animal.

10. The method of claim 1, wherein said administering improves the health of the aquatic animal by increasing the surface area of the intestinal villi of the aquatic animal.

11. The method of claim 1, wherein said administering improves the health of the aquatic animal by increasing length of the intestinal villi of the aquatic animal.

12. The method of claim 1, wherein said administering improves the health of the aquatic animal by maintaining healthy gut microflora in the aquatic animal.

13. The method of claim 1, wherein said administering improves the health of the aquatic animal by controlling pathogenic microorganisms in the gut of the aquatic animal.

14. The method of claim 1, wherein the extruded pellet further comprises the *Bacillus amyloliquefaciens* strain having the deposit accession number NRRL B-50349.

15. The method of claim 1, wherein the extruded pellet further comprises the *Bacillus subtilis* strain having the deposit accession number NRRL B-50605.

16. The method of claim 1, wherein the extruded pellet further comprises the *Bacillus pumilus* strain having the deposit accession number NRRL B-50016.

17. The method of claim 1, wherein the extruded pellet further comprises the *Bacillus amyloliquefaciens* strain having the deposit accession number NRRL B-50017.

18. The method of claim 1, wherein the extruded pellet further comprises the *Bacillus amyloliquefaciens* strain having the deposit accession number NRRL B-50141.

19. The method of claim 1, wherein the extruded pellet further comprises the *Bacillus amyloliquefaciens* strain having the deposit accession number NRRL B-50607.

20. The method of claim 1, wherein the extruded pellet further comprises the *Bacillus amyloliquefaciens* strain having the deposit accession number NRRL B-50151.

21. The method of claim 1, wherein the extruded pellet further comprises the *Bacillus subtilis* strain having the deposit accession number NRRL B-50606.

22. The method of claim 1, wherein the extruded pellet further comprises the *Bacillus subtilis* strain having the deposit accession number NRRL PTA-7547.

23. The method of claim 1, wherein the extruded pellet further comprises the *Bacillus amyloliquefaciens* strain having the deposit accession number NRRL B-50304.

24. The method of claim 1, wherein the extruded pellet further comprises the *Bacillus subtilis* strain having the deposit accession number NRRL B-50622.

* * * * *